United States Patent
Seo et al.

(10) Patent No.: US 9,263,194 B2
(45) Date of Patent: Feb. 16, 2016

(54) PORPHYRIN-PEPTOID CONJUGATE AND THE PREPARATION PROCESS THEREOF

(71) Applicant: GWANGJU INSTITUTE OF SCIENCE AND TECHNOLOGY, Gwangju (KR)

(72) Inventors: Jiwon Seo, Gwangju (KR); Bo Yeong Kang, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 14/199,317

(22) Filed: Mar. 6, 2014

(65) Prior Publication Data

US 2015/0073122 A1    Mar. 12, 2015

(30) Foreign Application Priority Data

Sep. 6, 2013  (JP) .................................. 2013-184961
Jan. 8, 2014  (KR) ........................ 10-2014-0002307

(51) Int. Cl.

| | | |
|---|---|---|
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *H01G 9/20* | (2006.01) |
| *H01L 51/00* | (2006.01) |
| *C07K 14/795* | (2006.01) |
| *C07K 14/00* | (2006.01) |
| *C07D 487/22* | (2006.01) |

(52) U.S. Cl.
CPC ............ *H01G 9/2059* (2013.01); *C07D 487/22* (2013.01); *C07K 14/001* (2013.01); *C07K 14/795* (2013.01); *H01L 51/0077* (2013.01); *H01L 51/0093* (2013.01)

(58) Field of Classification Search
CPC .... A61K 38/00; C07K 14/795; C07K 1/1077; C07K 7/06
See application file for complete search history.

(56) References Cited

PUBLICATIONS

Wu et al., J. Am. Chem. Soc., 2001, vol. 123, No. 13, published on Web Mar. 8, 2001.*
N-terminal Acetylation and C-terminal Amidation of Peptides, Technical Information, Thermo Electron Corp., 2004, 2 pages.*
Myung-Seok Choi et al., A Large Dendritic Multiporphyrin Array as a Mimic of the Bacterial Light-Harvesting Antenna Complex: Molecular Design of an Efficient Energy Funnel for Visible Photons, article, 2001, pg. 3194-3198, vol. 40, No. 17, Wiley-VCH Verlag GmbH.
Tina Schroder et al., Solid-Phase Synthesis, Bioconjugation, and Toxicology of Novel Cationic Oligopeptoids for Cellular Drug Delivery, 2007, 342-354, vol. 18, Bioconjugate Chem.
Korean Office Action dated May 26, 2015, citing the above reference(s).

* cited by examiner

*Primary Examiner* — James H Alstrum Acevedo
*Assistant Examiner* — Kaipeen Yang
(74) *Attorney, Agent, or Firm* — Hauptman Ham, LLP

(57) ABSTRACT

Disclosed are a porphyrin-peptoid conjugate and a method for preparing the same. The porphyrin-peptoid conjugate according to the present disclosure has porphyrins arranged face-to-face on a helical peptoid. The porphyrin-peptoid conjugate according to the present disclosure is a new-concept photosensitizing dye material wherein the distance, arrangement and number of porphyrins are controllable. Since the porphyrin-peptoid conjugate is monodisperse and has a precisely defined structure, selective decoration of dyes is easy and dyes can be arranged on the peptoid helix sequence and space specifically. Accordingly, a new high-efficiency photosensitizing dye molecule system having wide absorption spectrum including the visible and near-infrared range and high absorption coefficient can be prepared.

9 Claims, 22 Drawing Sheets peptide peptoid beta-peptide

Pitch: 6.7 Å
Periodicity: 3 residues/turn (a) Submonomer synthesis scheme

PORPHYRIN-PEPTOID CONJUGATE AND THE PREPARATION PROCESS THEREOF

CROSS-REFERENCE TO RELATED APPLICATIONS

This application claims priority under 35 U.S.C. §119 to Japanese Patent Application No. 2013-184961 filed on Sep. 6, 2013 in the Japanese Patent Office and Korean Patent Application No. 10-2014-0002307 filed on Jan. 8, 2014 in the Korean Intellectual Property Office, the disclosures of which are incorporated herein by reference in its entirety.

TECHNICAL FIELD

The present disclosure relates to a porphyrin-peptoid conjugate as a photosensitizing dye material for artificial photosynthesis and a method for preparing the same. More particularly, it relates to a porphyrin-peptoid conjugate wherein porphyrins bound to the side chains of a helical peptoid are arranged face-to-face and the distance between the porphyrins, arrangement thereof and number thereof are controlled.

BACKGROUND

Many researches are under way for commercialization of a dye-sensitized solar cell. Examples include technical development for synthesis of $TiO_2$ nanoparticles of various structures and for increasing the surface area thereof, development of new metal oxide electrodes, development of dyes and electrolytes having high efficiency and stability, and improvement of preparation processes. In particular, development of new photosensitizing dye materials that directly affect the efficiency of dye-sensitized solar cells is actively ongoing. Especially, in order to improve the overall efficiency of a dye-sensitized solar cell, improvement of the light harvesting efficiency of the dyes is important. As examples of such dyes, there are ruthenium (Ru) complexes, porphyrins, phthalocyanines and other various organic dyes.

Among them, porphyrins are actively studied because of their interesting photophysical and chemical properties. Since adequate arrangement of porphyrins leads to many interesting molecules useful as from sensors to new photoelectric materials, there are many efforts to establish defined oligomeric arrangement of porphyrins, especially, that mimics the naturally occurring photosynthetic antenna system. To provide desirable photoelectric properties in an artificial light-harvesting complex as the nature fully utilizes organized pigments in the light-harvesting complex, a higher-level arrangement of porphyrin dyes is necessary.

Up to now, the researches on the interaction between porphyrins have mostly focused on two π-planes arranged side-by-side. In contrast, there have been few researches on the face-to-face arrangement of porphyrins, probably because of the inability to synthesize an effective scaffold.

The development of artificial light-harvesting systems thus far has mainly been accomplished by binding a dye to a biopolymer or synthetic polymer material as a scaffold and forming a complex through self-assembly or binding on the surface of nanoparticles. However, the systems synthesized in this manner are mostly polydisperse complexes and it is not easy to precisely control the position where the dye is attached.

To solve this problem, an artificial light-harvesting system using a dendrimer as a scaffold was proposed. The light-harvesting system using the dendrimer has been used in many multi-pigment array light-harvesting systems because it is monodisperse and has a precisely-defined structure.

However, there are problems that the synthetic yield of the dendrimer is low and it is difficult to arrange two different dyes at desired positions of one dendrimer molecule (non-patent document 1).

Use of the face-to-face arrangement of porphyrins as a scaffold has never been reported.

REFERENCE OF THE RELATED ART

Non-Patent Document

1. Choi, M.; Aida, T.; Yamazaki, T.; Yamazaki, I. Angew. Chem., Int. Ed. 2001, 40, 3194.

SUMMARY

The present disclosure is directed to providing a porphyrin-peptoid conjugate wherein the distance, arrangement and number of photosensitizing dyes are controlled.

The present disclosure is also directed to providing a method for preparing a porphyrin-peptoid conjugate, which involves a simple process and is inexpensive.

In one general aspect, the present disclosure provides a porphyrin-peptoid conjugate wherein porphyrins bound to the side chains of a helical peptoid are arranged face-to-face.

In another general aspect, the present disclosure provides a conjugate represented by Chemical Formula 1, which has a helical structure and wherein T's are arranged face-to-face:

[Chemical Formula 1]

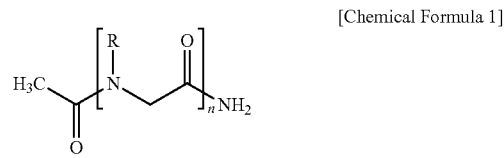

wherein n is 9 or 12,

R is $R_1$ or $R_2$, $R_1$ is

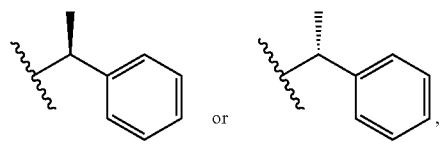

$R_2$ is selected from

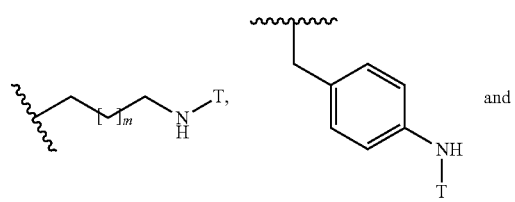

and

-continued

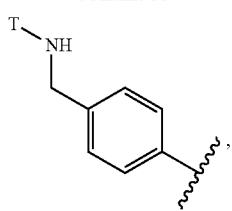

m is an integer from 1 to 5,

T is selected from

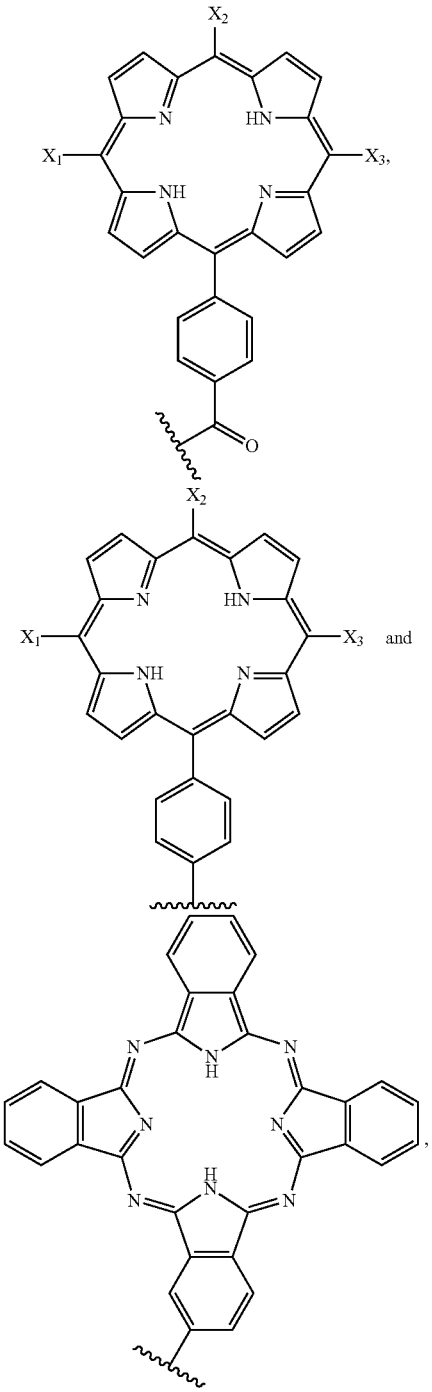

each of $X_1$, $X_2$, $X_3$, which are identical or different, is

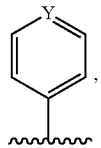

Y is selected from C—H, N, C—COOH, C—$SO_3H$ and C—$NH_2$, and the tilde symbol indicates a chemical bond.

In another general aspect, the present disclosure provides a method for preparing a porphyrin-peptoid conjugate, including:

(a) preparing a helical peptoid by microwave-assisted solid-phase synthesis according to the submonomer protocol;

(b) acetylating the N-terminal amine of the helical peptoid;

(c) removing a methoxytrityl (Mmt) group from the N-terminal acetylated helical peptoid by treating repeatedly with trifluoroacetic acid (TFA);

(d) preparing tetraphenylporphyrin (TPP) carboxylic acid according to the Lindsey's protocol;

(e) preparing TTP-NHS ester by esterifying the tetraphenylporphyrin (TPP) carboxylic acid; and (f) conjugating the TPP-NHS ester with the methoxytrityl (Mmt)-removed helical peptoid.

The porphyrin-peptoid conjugate according to the present disclosure has porphyrins arranged face-to-face on a helical peptoid. The porphyrin-peptoid conjugate according to the present disclosure is a new-concept photosensitizing dye material wherein the distance, arrangement and number of porphyrins are controllable. Since the porphyrin-peptoid conjugate is monodisperse and has a precisely defined structure, selective decoration of dyes is easy and dyes can be arranged on the peptoid helix sequence and space specifically. Accordingly, a new high-efficiency photosensitizing dye molecule system having wide absorption spectrum including the visible and near-infrared range and high absorption coefficient can be prepared.

Therefore, an artificial light-harvesting system with improved efficiency can be prepared.

BRIEF DESCRIPTION OF DRAWINGS

The above and other objects, features and advantages of the present disclosure will become apparent from the following description of certain exemplary embodiments given in conjunction with the accompanying drawings, in which.

DETAILED DESCRIPTION OF EMBODIMENTS

Hereinafter, exemplary embodiments will be described in detail with reference to the accompanying drawings and examples. However, the scope of the present disclosure is not limited by the drawings and examples.

In an aspect, the present disclosure provides a conjugate represented by Chemical Formula 1, which has a helical structure and wherein T's are arranged face-to-face:

[Chemical Formula 1]

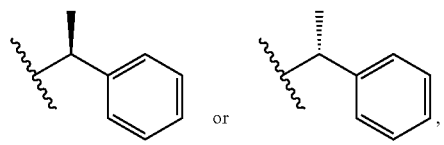

wherein
n is 9 or 12,
R is $R_1$ or $R_2$,
$R_1$ is

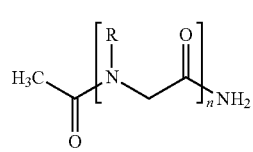

or , $R_2$ is selected from

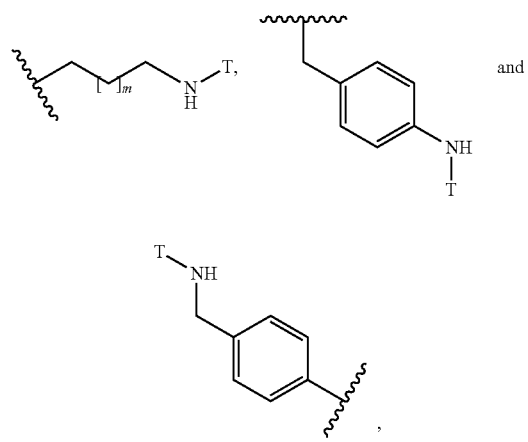

m is an integer from 1 to 5,
T is selected from

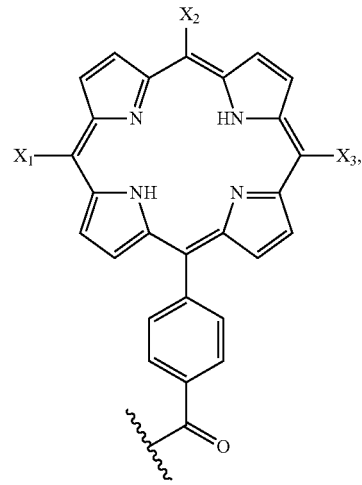

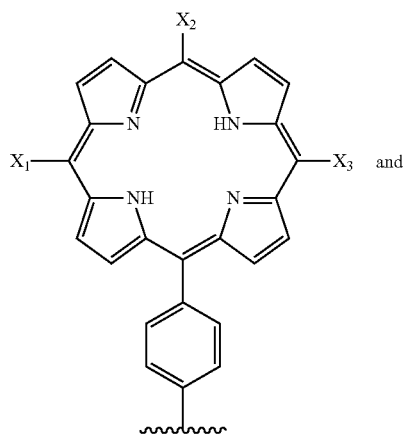

and

-continued

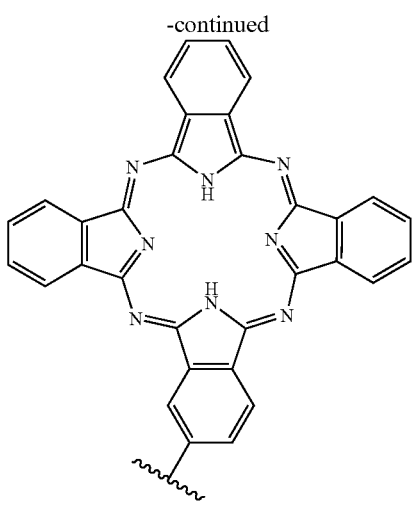

each of $X_1$, $X_2$, $X_3$, which are identical or different, is

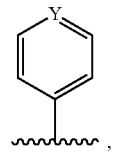

Y is selected from C—H, N, C—COOH, C—SO$_3$H and C—NH$_2$, and
the tilde symbol indicates a chemical bond.

In an exemplary embodiment, the conjugate of the present disclosure has a structure selected from Chemical Formulas 2-5:

[Chemical Formula 2]

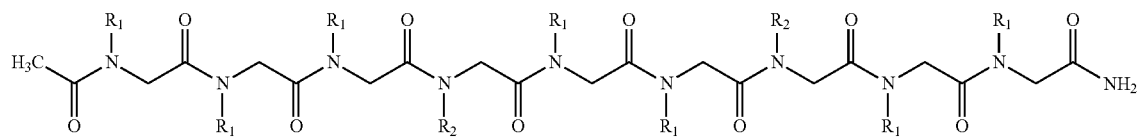

[Chemical Formula 3]

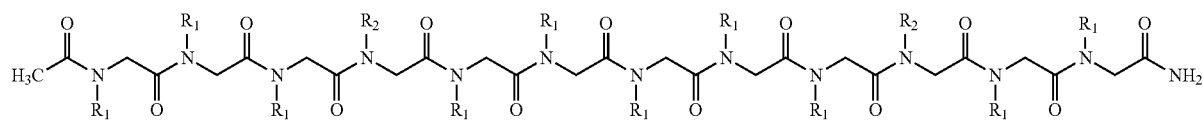

[Chemical Formula 4]

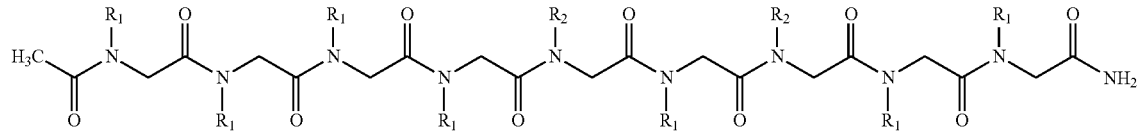

[Chemical Formula 5]

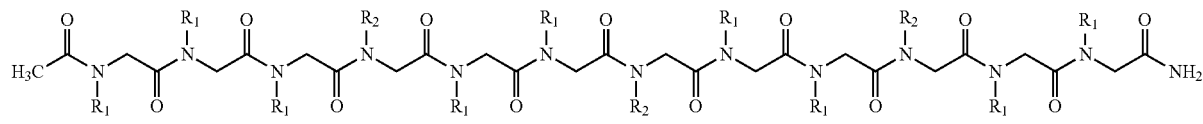

In another exemplary embodiment, the conjugate has a structure selected from Chemical Formulas 6-9:

[Chemical Formula 6]

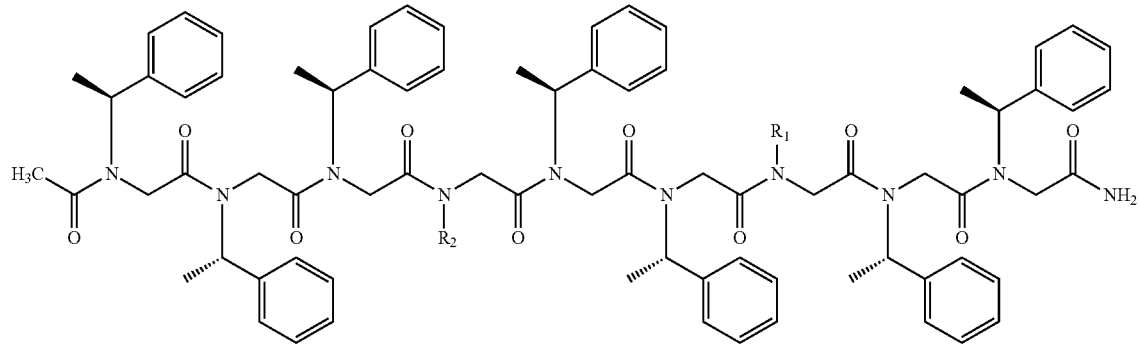

[Chemical Formula 7]
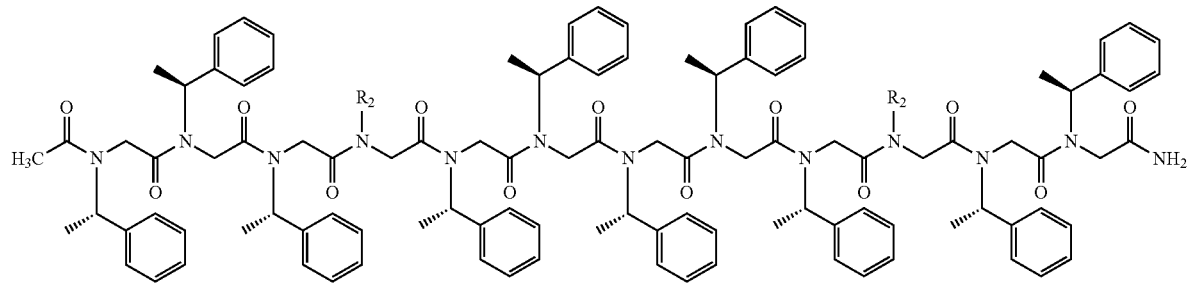
[Chemical Formula 8]
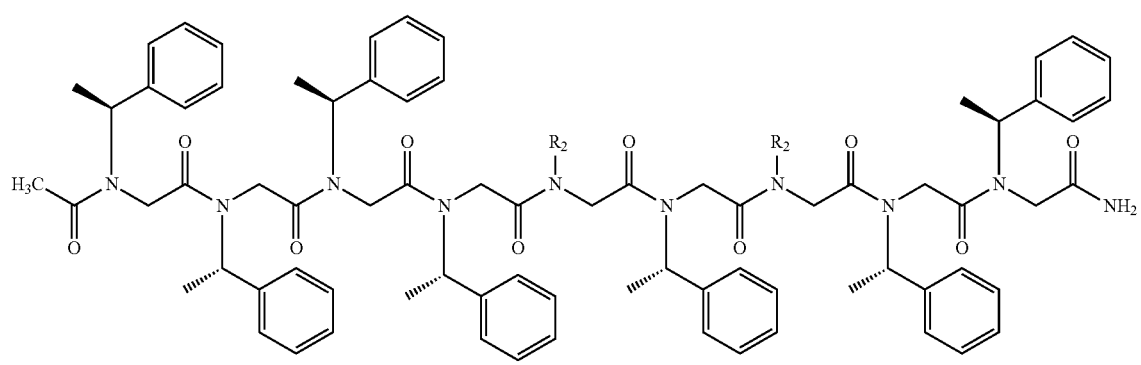
[Chemical Formula 9]
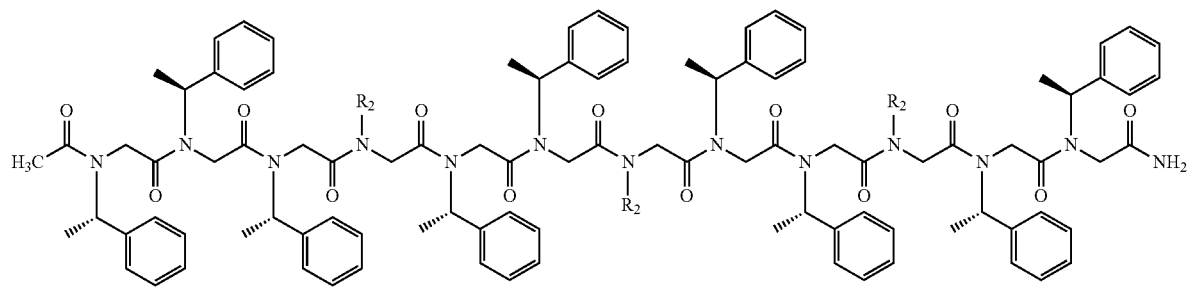
In another exemplary embodiment, $R_2$'s may have the same structure. In another exemplary embodiment, the conjugate has a structure selected from Chemical Formulas 10-13:
[Chemical Formula 10]
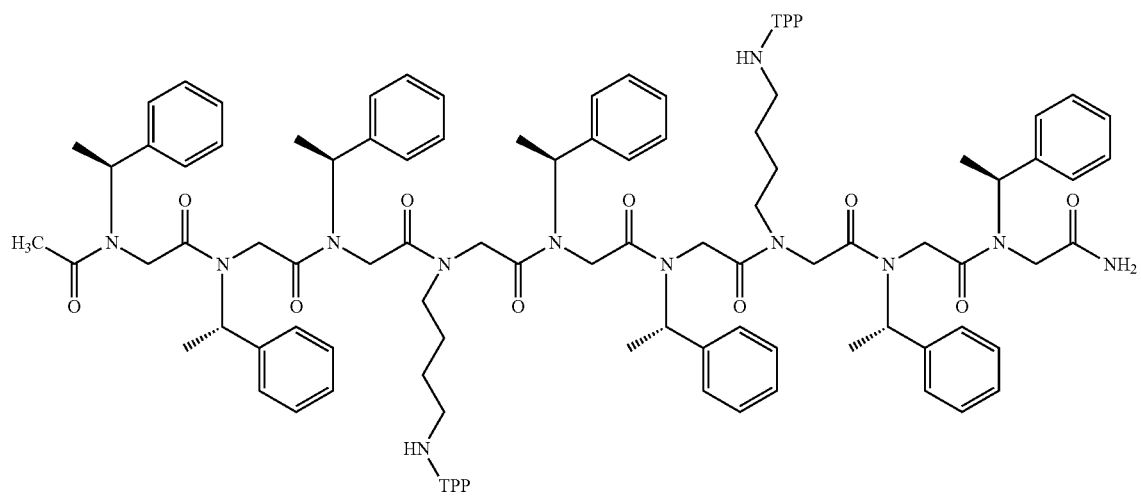

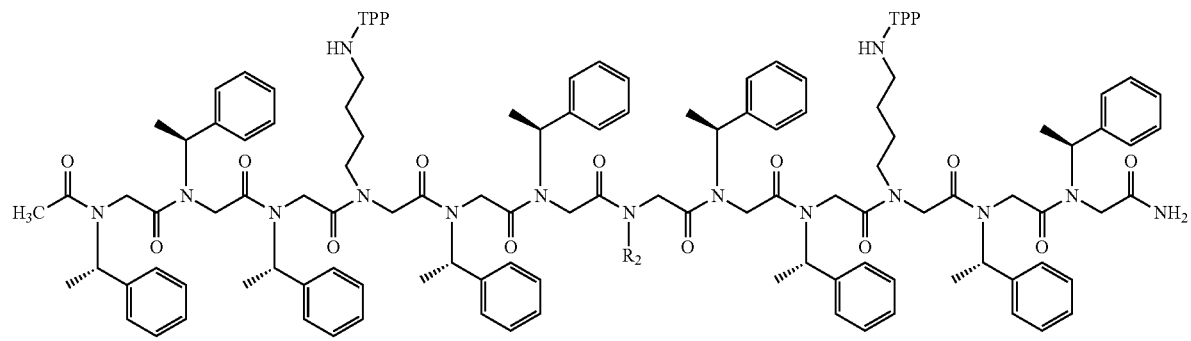
[Chemical Formula 11]
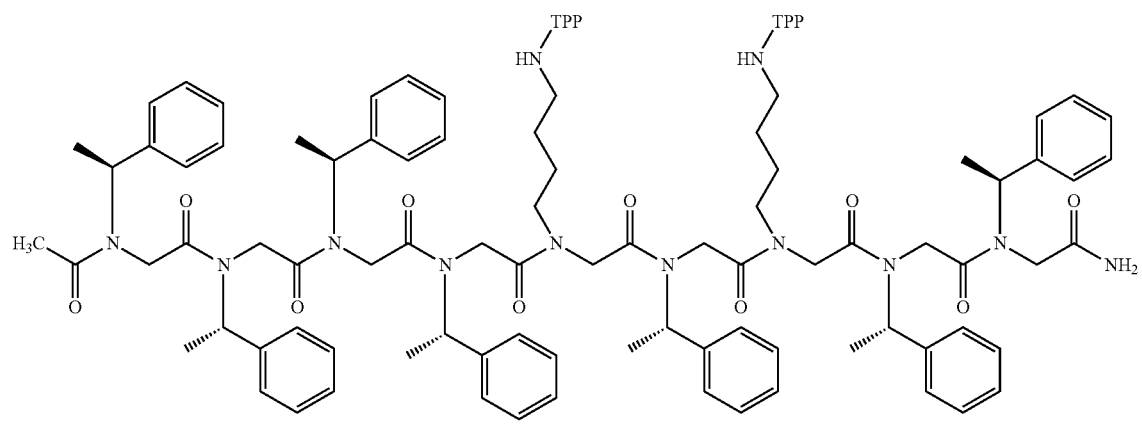
[Chemical Formula 12]
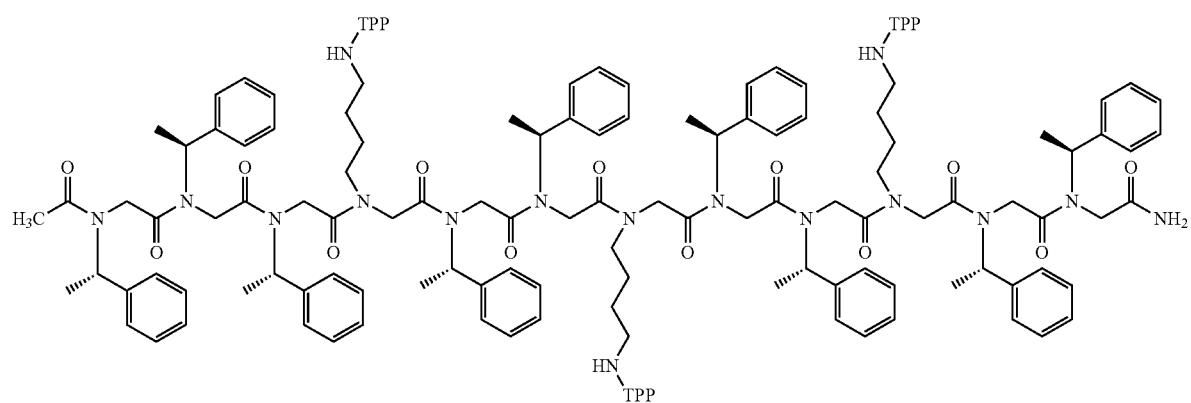
[Chemical Formula 13]

wherein
TPP represents

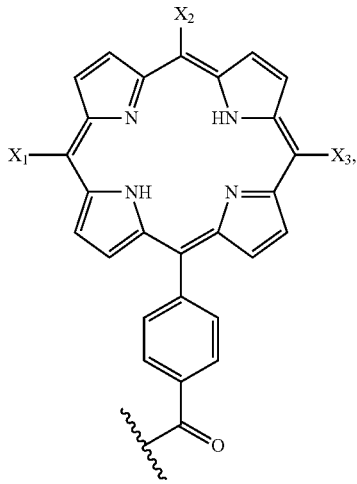

each of $X_1$, $X_2$ and $X_3$ is

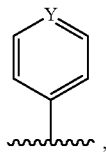

Y is C—H, and
the tilde symbol indicates a chemical bond.

In another general aspect, the present disclosure provides a method for preparing a porphyrin-peptoid conjugate, including:

(a) preparing a helical peptoid by microwave-assisted solid-phase synthesis according to the submonomer protocol;

(b) acetylating the N-terminal amine of the helical peptoid;

(c) removing a methoxytrityl group from the N-terminal acetylated helical peptoid by treating repeatedly with trifluoroacetic acid (TFA);

(d) preparing tetraphenylporphyrin (TPP) carboxylic acid according to the Lindsey's protocol;

(e) preparing TTP-NHS ester by esterifying the tetraphenylporphyrin (TPP) carboxylic acid; and (f) conjugating the TPP-NHS ester with the methoxytrityl-removed helical peptoid.

In an exemplary embodiment, the present disclosure provides a method for preparing a porphyrin-peptoid conjugate, which further includes purifying the porphyrin-peptoid conjugate by reversed-phase HPLC.

The porphyrin-peptoid conjugate according to the present disclosure uses a peptoid having the following characteristics as a scaffold to overcome the above-described problems of the prior art.

Figure 1:
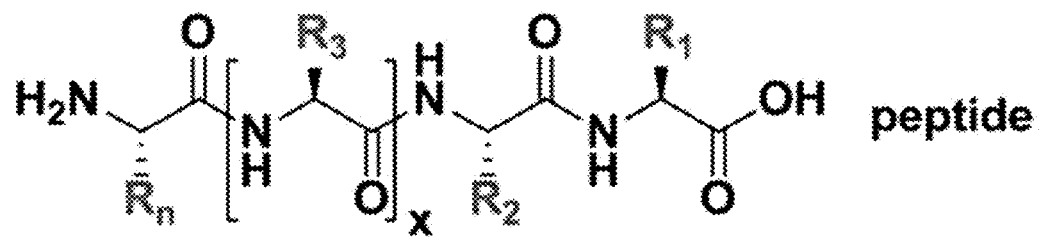
FIG. 1 shows the structures of a peptide, a peptoid and a β-peptide.
Figure 1:
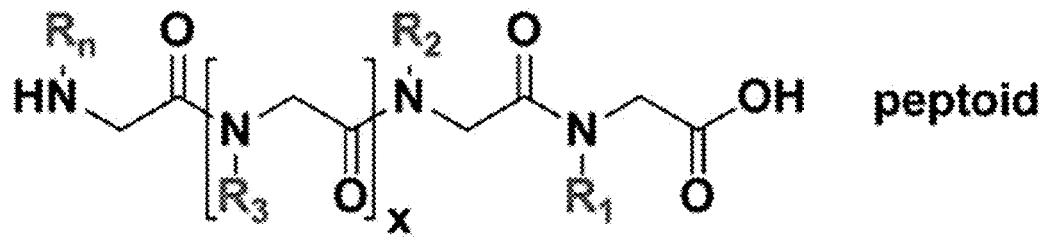
Figure 1:
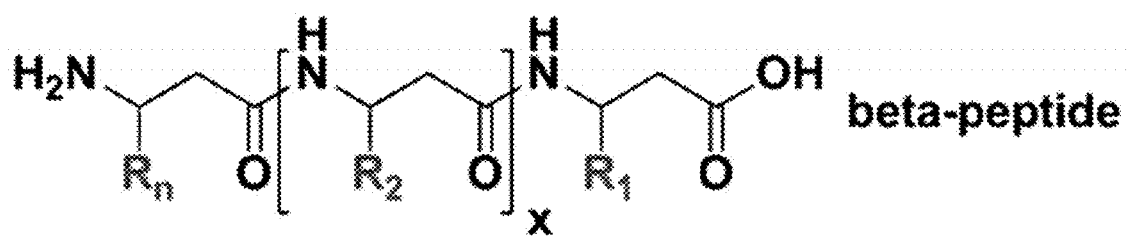

FIG. 1 shows the structures of a peptide, a peptoid and a β-peptide. Referring to FIG. 1, the most important feature of a biopolymer (e.g., protein or nucleic acid) is the sequence specificity. Monomers having basic information give rise to precisely defined sequences, and a specific structure is formed as the sequences are folded or assembled. The resulting structure determines the functionality of a biopolymer.

Figure 2:
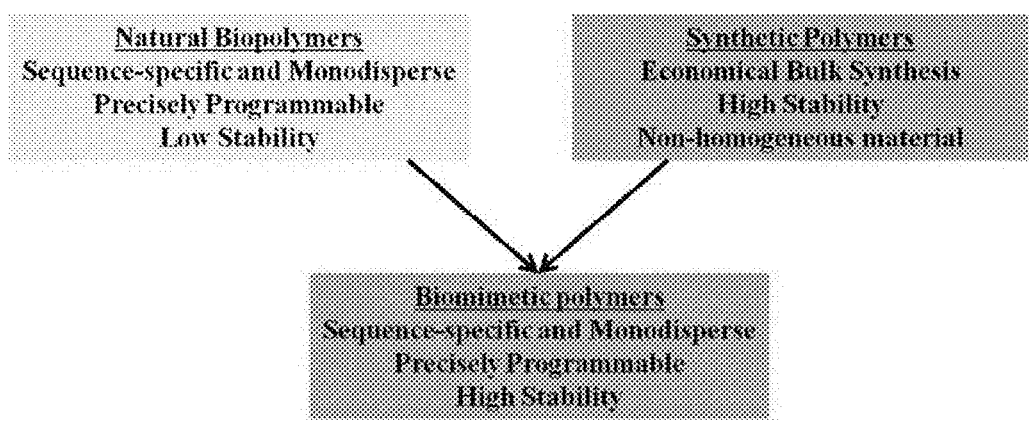
FIG. 2 shows the data comparing the characteristics of biomimetic polymers, biopolymers and synthetic polymers.

FIG. 2 compares the characteristics of biomimetic polymers, biopolymers and synthetic polymers. Referring to FIG. 2, biomimetic polymers such as peptoids or β-peptides are relatively new materials and have characteristics intermediate between those of biopolymers and synthetic polymers. For example, since a peptoid is monodisperse and has sequence specificity, precise control of chain length, side-chain functional groups and monomer sequence is possible and high stability is ensured against proteolysis. Accordingly, the sequence specificity and stability of biomimetic polymers can be advantageous in the development of new materials.

Peptoids are peptide derivatives having oligo-N-substituted glycine as the basic unit. They are novel materials developed to mimic proteins. Peptoids having precisely defined sequence and chain length can be prepared easily through submonomer synthesis. With the present synthesis technology, peptoids having 50 monomer units (5-7 kDa) can be synthesized without special difficulty.

Figure 3:
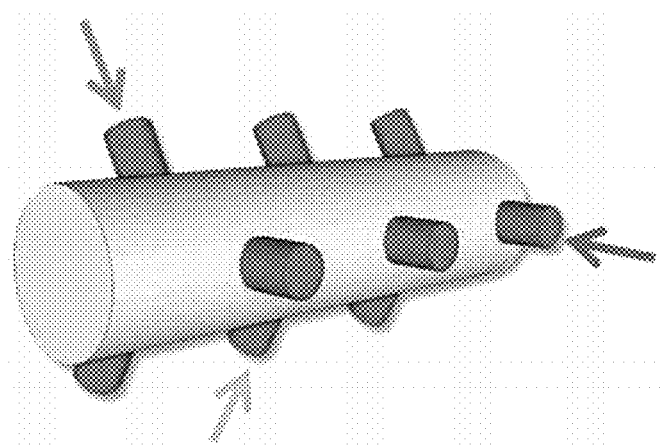
FIG. 3 shows the structural characteristics of a helical peptoid.

FIG. 3 shows the structural characteristics of a helical peptoid. Referring to FIG. 3, the helical structure of a peptoid is formed not by hydrogen bonding, as in the naturally occurring peptides, but by steric repulsion. As a result, it is structurally stable even under extreme conditions such as high temperature (>100° C.), high salt concentration, etc. Peptoids adopt a polyproline-type I (PPI)-like conformation. That is to say, they exhibit periodicity with three residues per turn and a pitch of about 6 Å. These structural characteristics are advantageous in designing of materials having peptoid helical structures as backbones not only in sequence alignment but also in spatial arrangement.

The porphyrin-peptoid conjugate according to the present disclosure has porphyrins arranged face-to-face on a helical peptoid. The porphyrin-peptoid conjugate has a monodisperse scaffold and easily controllable structure and the distance, arrangement and number of the porphyrins can also be controlled. Accordingly, a photosensitizing dye complex molecule using the same can have improved efficiency.

Figure 4:
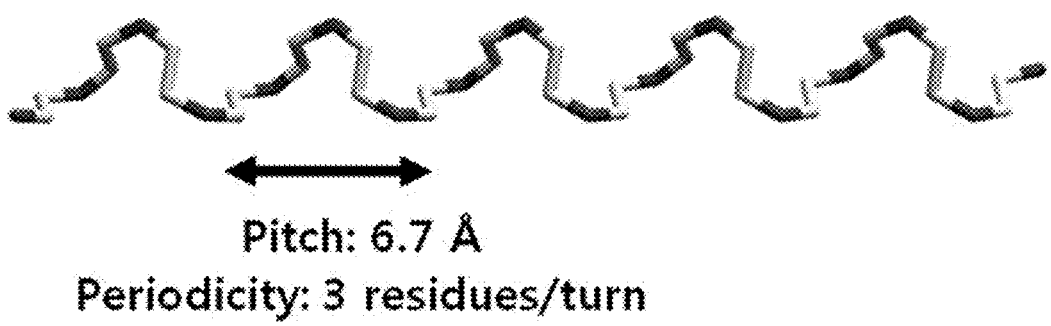
FIG. 4 schematically shows a control peptide wherein functional groups can be spatially arranged at desired positions through selective decoration.
Figure 5:
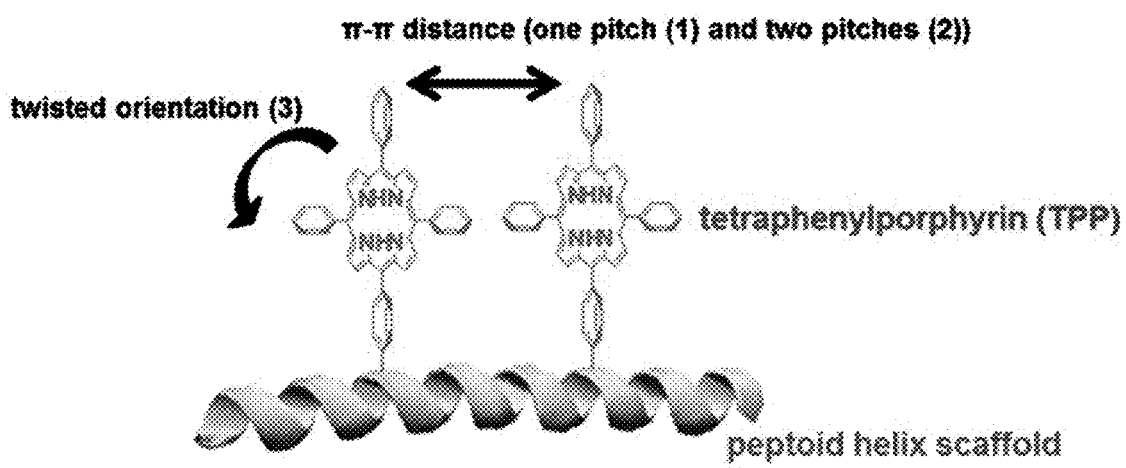
FIG. 5 schematically shows the design of a porphyrin-peptoid conjugate (hereinafter, "PPC")

FIG. 4 schematically shows a control peptoid wherein functional groups can be spatially arranged at desired positions through selective decoration. FIG. 5 schematically shows the design of a porphyrin-peptoid conjugate (PPC).

Referring to FIG. 4 and FIG. 5, the porphyrin-peptoid conjugate (PPC) of FIG. 5 can be prepared using the control peptoid of FIG. 4 as a scaffold. To describe in more detail, the control peptoid (peptoid oligomer) can be prepared to have a helical structure using specific monomers. Since the peptoid has a spatially well-defined secondary structure, functional groups can be conjugated at the side chains of desired positions. The 'selective decoration' of attaching the wanted functional groups at the peptoid side chains of selective positions is one of the core technologies necessary to embody the present disclosure.

As seen from FIG. 5, a porphyrin-peptoid conjugate (PPC) with controlled distance, relative arrangement and number of dyes can be designed according to the present disclosure through selective decoration. The PPC of the present disclosure can be synthesized to have a wanted number of dyes at desired positions with desired relative arrangement, which has not been resolved through the existing molecular design.

The porphyrin-peptoid conjugate according to the present disclosure can be one of Chemical Formulas 10-13.

[Chemical Formula 10]
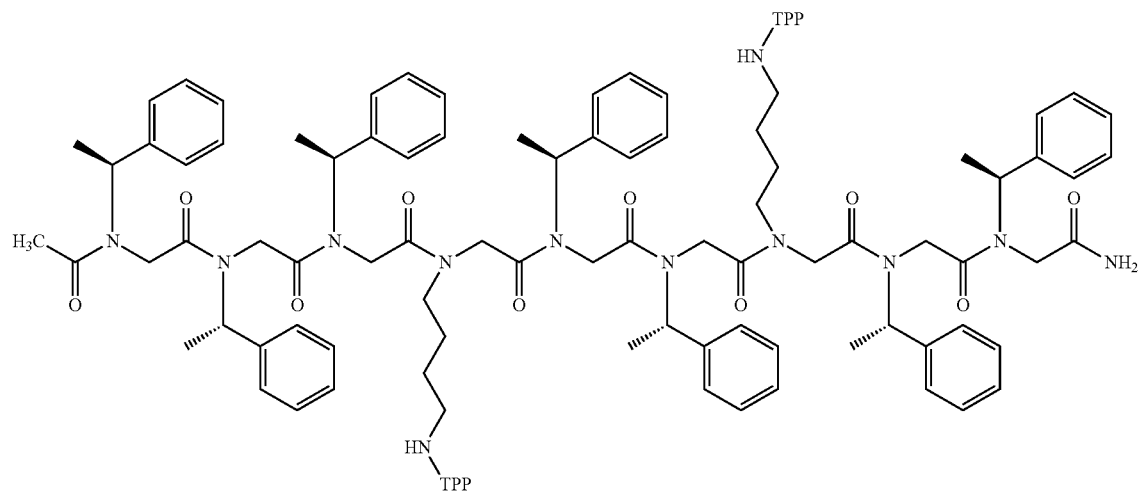
[Chemical Formula 11]
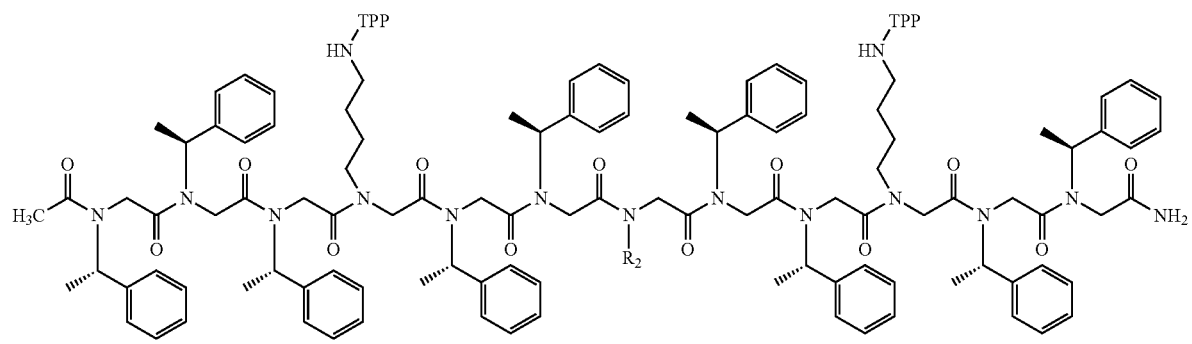
[Chemical Formula 12]
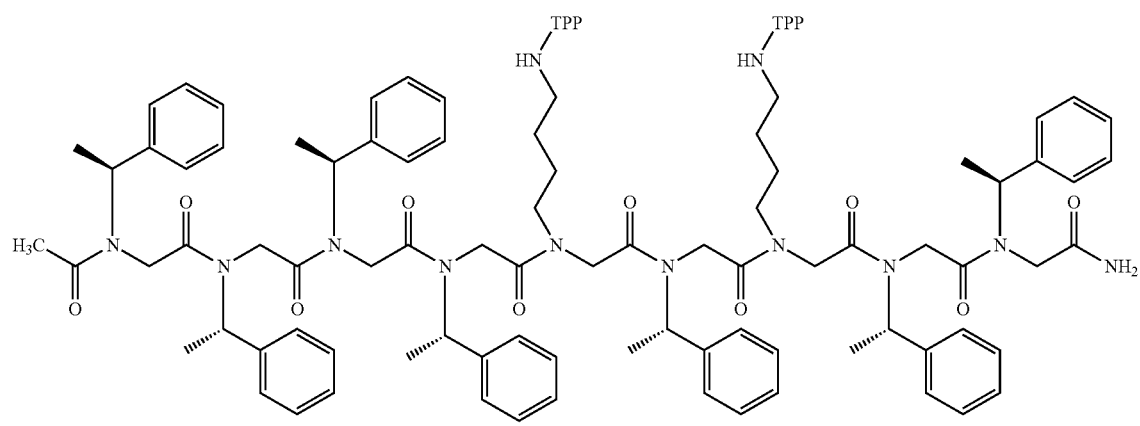

-continued

[Chemical Formula 13]

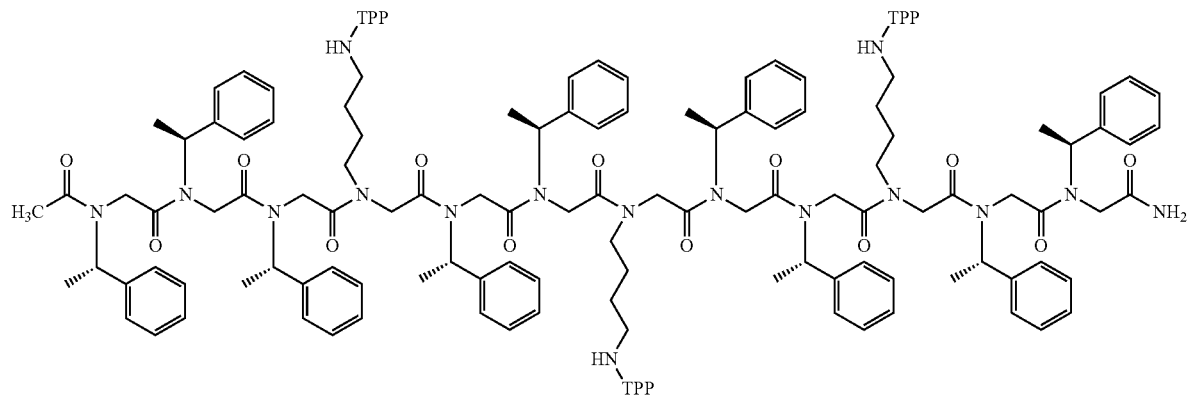

Figure 6A:
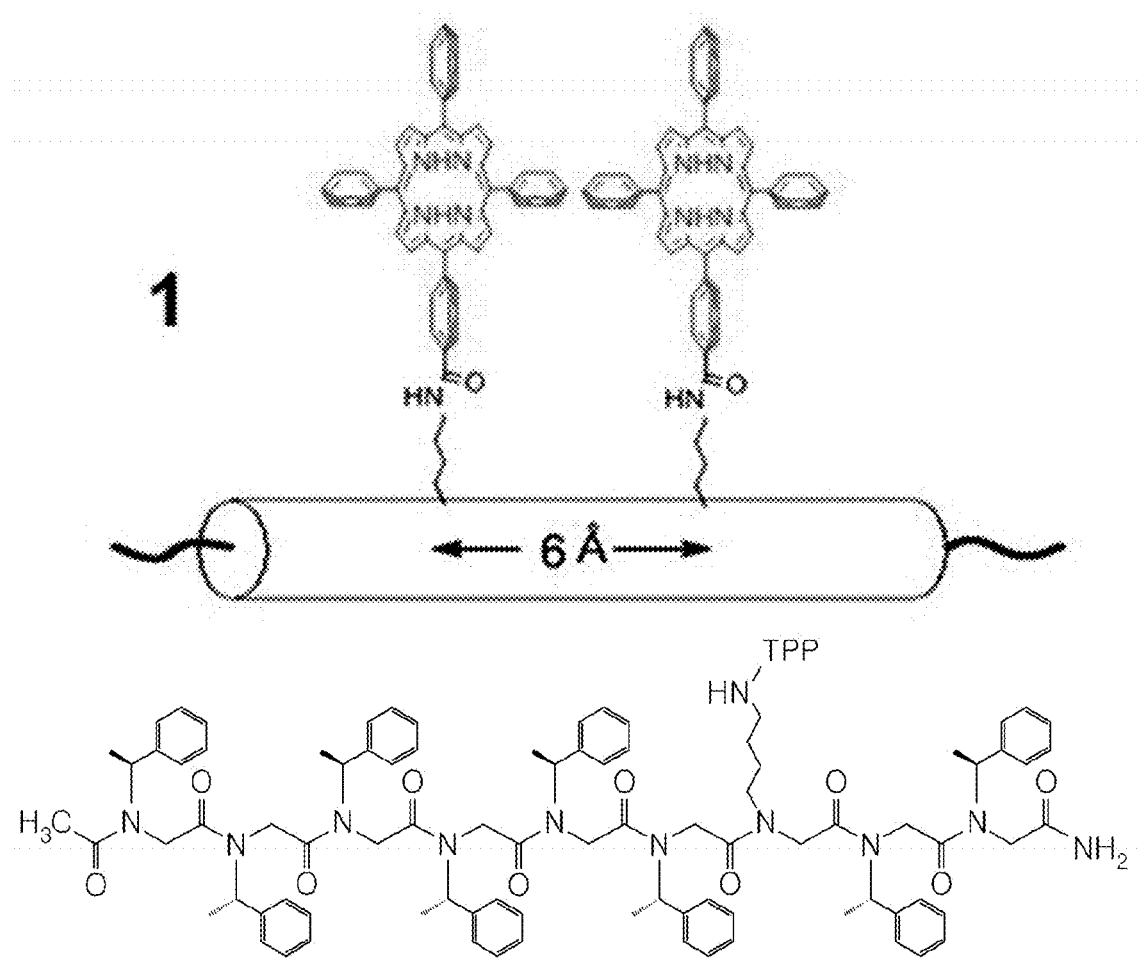
FIG. 6a shows a PPC according to an exemplary embodiment of the present disclosure wherein the distance between two porphyrins is one pitch.

FIG. 6a shows a PPC according to an exemplary embodiment of the present disclosure wherein the distance between two porphyrins is one pitch.

Figure 6B:
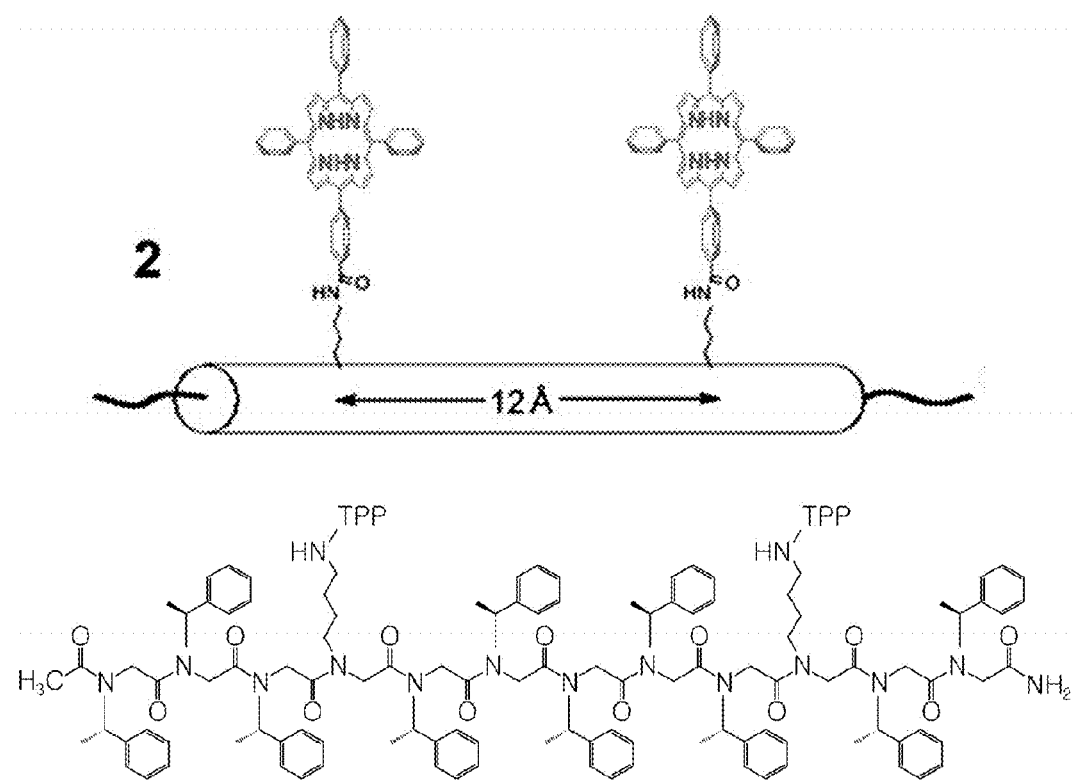
FIG. 6b shows a PPC according to an exemplary embodiment of the present disclosure wherein the distance between two porphyrins is two pitches.

FIG. 6b shows a PPC according to an exemplary embodiment of the present disclosure wherein the distance between two porphyrins is two pitches.

Figure 6C:
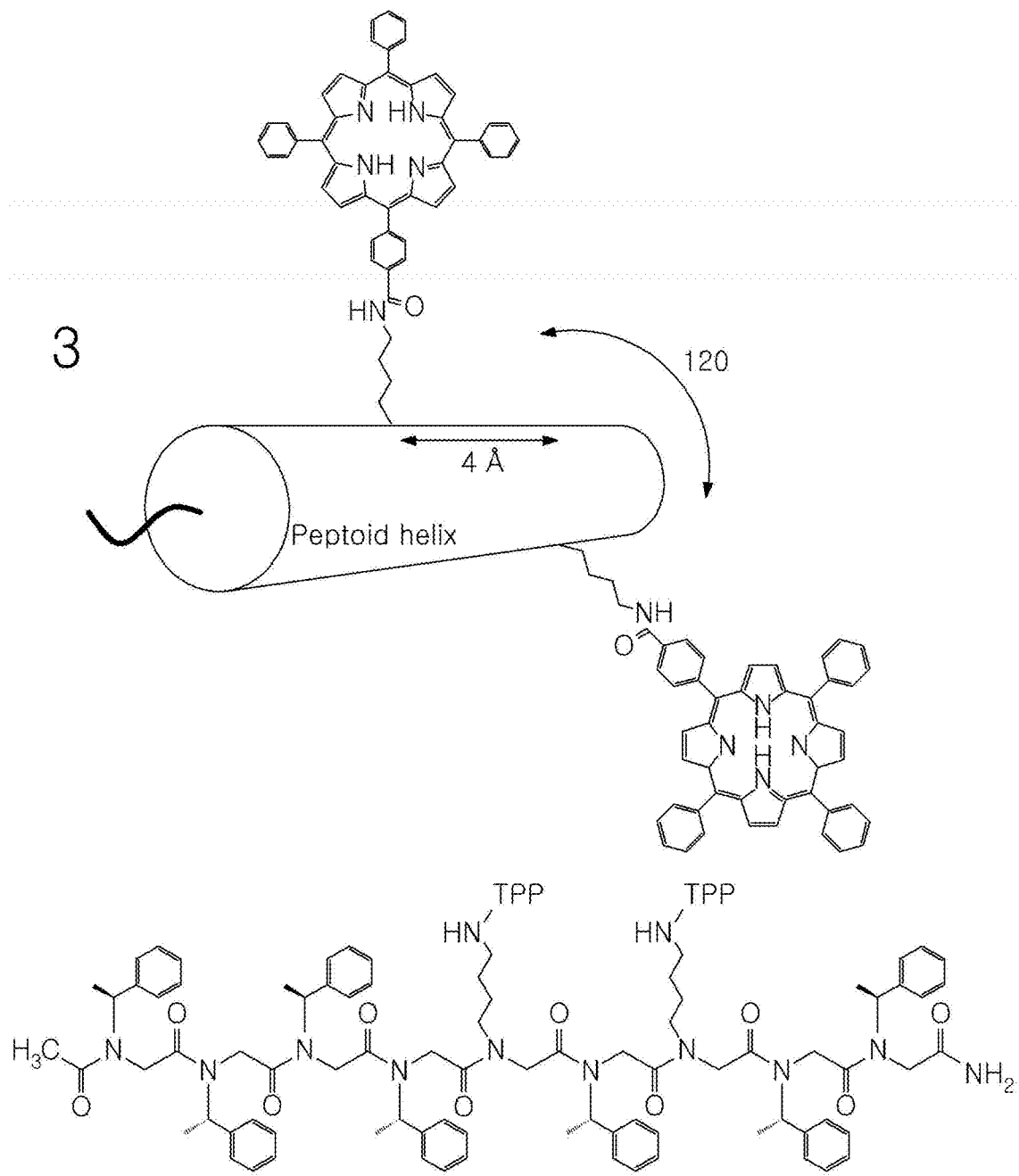
FIG. 6c shows a PPC according to an exemplary embodiment of the present disclosure wherein the relative arrangement of porphyrins is controlled.

FIG. 6c shows a PPC according to an exemplary embodiment of the present disclosure wherein the relative arrangement of porphyrins is controlled.

Figure 6D:
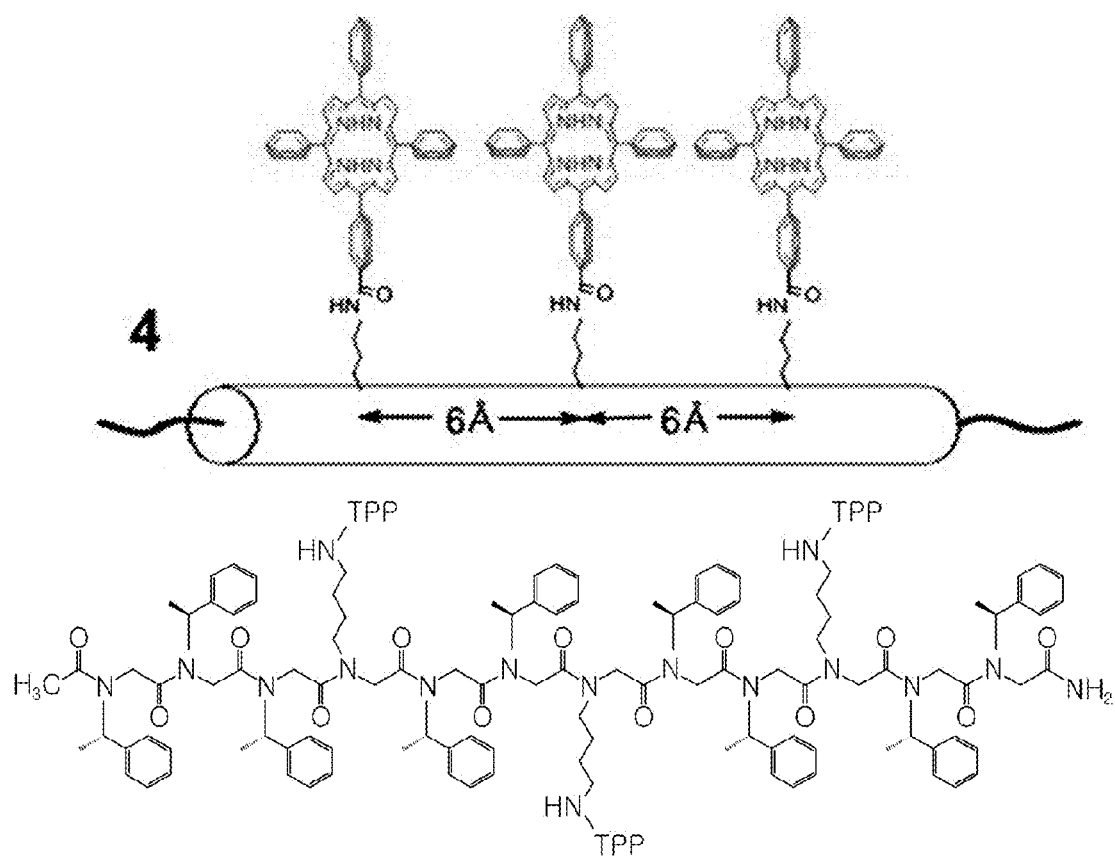
FIG. 6d shows a PPC according to an exemplary embodiment of the present disclosure wherein the distance between three porphyrins is two pitches.

FIG. 6d shows a PPC according to an exemplary embodiment of the present disclosure wherein the distance between three porphyrins is two pitches.

Referring to FIGS. 6a-6d, it can be seen that the distance, arrangement and number of porphyrins conjugated at peptoid side chains can be controlled. To describe in more detail, FIG. 6a shows a PPC wherein two porphyrins are arranged to be separated by one pitch, and FIG. 6b shows a PPC wherein two porphyrins are arranged to be separated by two pitches. FIG. 6c shows a PPC wherein the relative arrangement of two porphyrins is controlled as a slipped cofacial arrangement. FIG. 6d shows a PPC wherein three porphyrins are arranged.

From FIG. 6a and FIG. 6b, it can be seen that the distance between porphyrins is controllable. From FIG. 6a and FIG. 6c, it can be seen that the relative arrangement of porphyrins is also controllable. And, from FIG. 6a and FIG. 6d, it can be seen that the number of porphyrins is controllable. The PPCs with controlled distance, arrangement and number of porphyrins can be prepared by precisely controlling the sequence of the corresponding control peptoid. This will be described in detail later in examples and comparative examples.

Table 1 shows the sequence of porphyrin-peptoid conjugates according to exemplary embodiments of the present disclosure (Examples 1-4), the sequence of control peptoids thereof (Comparative Examples 1-4) and the sequence of an unstructured peptoid (Comparative Example 5).

TABLE 1

| | Chain length | Sequence |
|---|---|---|
| Ex. 1 | 9 | Ac-Nspe-Nspe-Nspe-Nlys(TPP)-Nspe-Nspe-Nlys(TPP)-Nspe-Nspe-NH₂ |
| Ex. 2 | 12 | Ac-Nspe-Nspe-Nspe-Nlys(TPP)-Nspe-Nspe-Nspe-Nspe-Nlys(TPP)-Nspe-Nspe-NH₂ |

TABLE 1-continued

| | Chain length | Sequence |
|---|---|---|
| Ex. 3 | 9 | Ac-Nspe-Nspe-Nspe-Nspe-Nlys(TPP)-Nspe-Nlys(TPP)-Nspe-Nspe-NH₂ |
| Ex. 4 | 12 | Ac-Nspe-Nspe-Nspe-Nlys(TPP)-Nspe-Nspe-Nlys(TPP)-Nspe-Nspe-Nlys(TPP)-Nspe-Nspe-NH₂ |
| Comp. Ex. 1 | 9 | Ac-Nspe-Nspe-Nspe-Nlys-Nspe-Nspe-Nlys-Nspe-Nspe-NH₂ |
| Comp. Ex. 2 | 12 | Ac-Nspe-Nspe-Nspe-Nlys-Nspe-Nspe-Nspe-Nspe-Nlys-Nspe-Nspe-NH₂ |
| Comp. Ex. 3 | 9 | Ac-Nspe-Nspe-Nspe-Nspe-Nlys-Nspe-Nlys-Nspe-Nspe-NH₂ |
| Comp. Ex. 4 | 12 | Ac-Nspe-Nspe-Nspe-Nlys-Nspe-Nspe-Nlys-Nspe-Nspe-Nspe-Nlys-Nspe-Nspe-NH₂ |
| Comp. Ex. 5 | 9 | Ac-Npm-Npm-Npm-Nlys(TPP)-Npm-Npm-Nlys(TPP)-Npm-Npm-NH₂ |

[Chemical Formula 14]

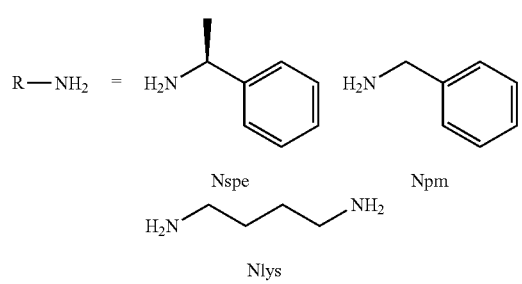

As seen from Table 1, the peptoids prepared in the examples and comparative examples exhibit sequence specificity because they are prepared by microwave-assisted solid-phase synthesis according to the submonomer protocol. In the sequence of control peptoids (Comparative Examples 1-4) and the sequence of PPCs (Examples 1-4), Ac means that the N-terminal amine has acetylated after a desired sequence is obtained to control the length of the control peptoids and PPCs. Nspe ((S)-(-)-1-phenylethylamine) is used to induce helical folding, and Nlys (1,4-diaminobutane) is used to conjugate porphyrins. That is to say, Comparative Example 1 is a control peptoid of Example 1, Comparative Example 2 is a control peptoid of Example 2, Comparative Example 3 is a control peptoid of Example 3, and Comparative Example 4 is a control peptoid of Example 4. Comparative Example 5 is an unstructured peptoid wherein Npm (benzylamine) is used instead of Nspe.

Nspe, Nlys and Npm are primary amines used to prepare the peptoids. Details will be described later with regard to the preparation process.

It can be seen that selective decoration is possible by controlling the position and number of Nlys on the control peptoid sequence. This means that PPCs having a desired number of dyes at desired positions with desired relative arrangement can be synthesized.

Although TTP is used in an exemplary embodiment of the present disclosure, it may be replaced by any one selected from the materials represented by Chemical Formulas 15-17, which have similar structures as TTP.

[Chemical Formula 15]

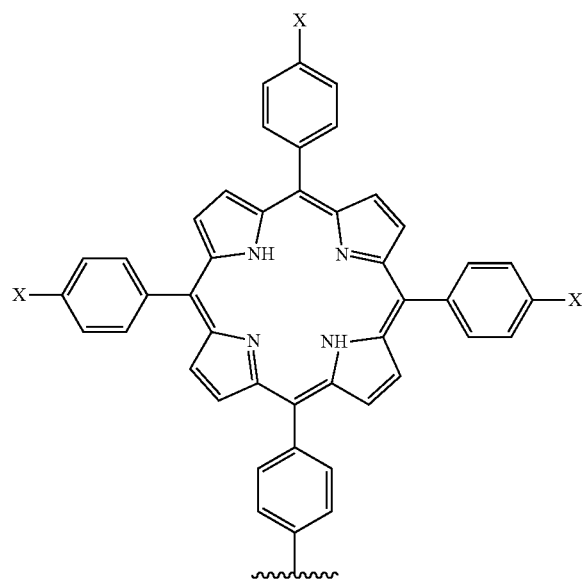

[Chemical Formula 16]

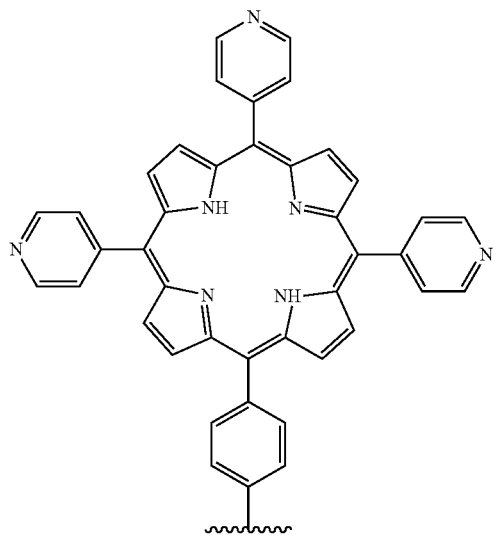

[Chemical Formula 17]

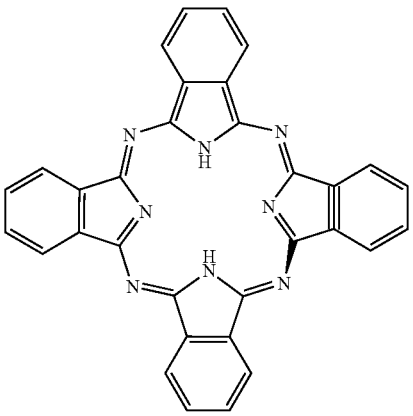

In Chemical Formula 15, X is selected from H, COOH, $SO_3H$ and $NH_2$.

The primary amines used in the present disclosure become the side chains of peptoids. Nspe, one of the side chains of helical peptoids represented by Chemical Formulas 10-13, can be replaced by Nrpe. The chemical formula of Nrpe is as follows.

[Chemical Formula 18]

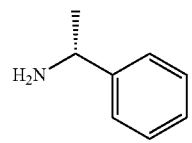

And, Nlys, one of the side chains of helical peptoids represented by Chemical Formulas 10-13, can be replaced by one selected from diaminopropane, diaminopentane or 4-(aminomethyl)aniline. The chemical structures of Nlys, diaminopropane, diaminorentane and 4-(aminomethyl) aniline are as follows.

[Chemical Formula 19]

[Chemical Formula 20]

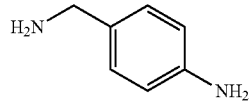

Chemical Formula 19 is the chemical formula of diaminopropane (n=1), diaminobutane (Nlys) (n=2) and diaminopentane (n=3).

And, Chemical Formula 20 is the chemical formula of 4-(aminomethyl)aniline.

Accordingly, the porphyrin-peptoid conjugate of the present disclosure can be prepared by using primary amines selected from Nspe or Nrpe as side chains for maintaining the helical structure and using primary amines selected from Nlys, diaminopropane, diaminorentane or 4-(aminomethyl) aniline as side chains for conjugation with porphyrins. The sequence of the primary amines may be controlled such that the porphyrin-peptoid conjugate is monodisperse.

The present disclosure also provides a method for preparing a porphyrin-peptoid conjugate, including:

(a) preparing a helical peptoid by microwave-assisted solid-phase synthesis according to the submonomer protocol;

(b) acetylating the N-terminal amine of the helical peptoid;

(c) removing a methoxytrityl (Mmt) group from the N-terminal acetylated helical peptoid by treating repeatedly with trifluoroacetic acid (TFA);

(d) preparing tetraphenylporphyrin (TPP) carboxylic acid according to the Lindsey's protocol;

(e) preparing TTP-NHS ester by esterifying the tetraphenylporphyrin (TPP) carboxylic acid; and (f) conjugating the TPP-NHS ester with the methoxytrityl (Mmt)-removed helical peptoid.

Figure 7A:
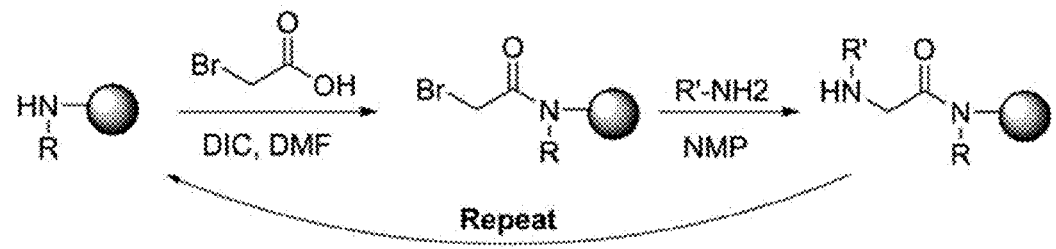
FIG. 7a describes submonomer synthesis.

FIG. 7a describes submonomer synthesis.

Figure 7B:
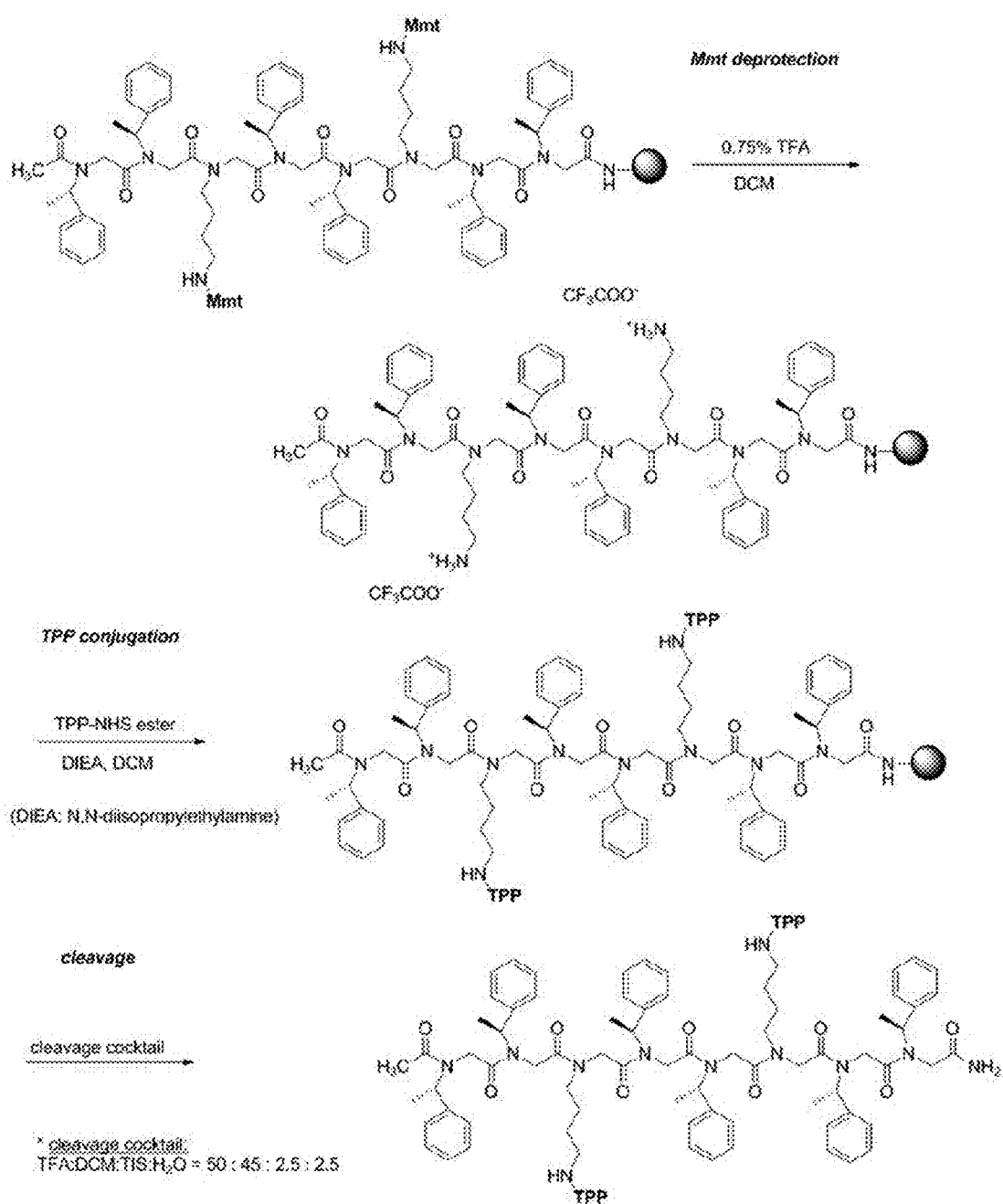
FIG. 7b schematically describes the synthesis of a porphyrin-peptoid conjugate.

FIG. 7b schematically describes the synthesis of a porphyrin-peptoid conjugate.

Figure 7C:
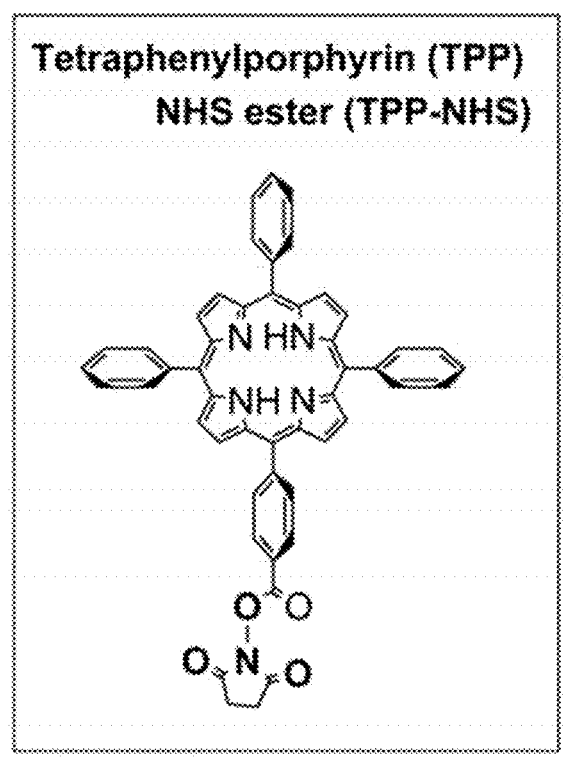
FIG. 7c shows TPP-NHS ester.

And, FIG. 7c shows TPP-NHS ester.

Hereinafter, the preparation method will be described in detail referring to FIGS. 7a-7c.

A desired control peptoid is prepared by microwave-assisted solid-phase synthesis according to the submonomer protocol and tetraphenylporphyrin (TPP) carboxylic acid is prepared according to the Lindsey's protocol. TTP-NHS ester is prepared by esterifying the tetraphenylporphyrin (TPP) carboxylic acid, and a porphyrin-peptoid conjugate is prepared by conjugating the control peptoid with the TTP-NHS ester.

<Preparation of Helical Peptoid by Microwave-Assisted Solid-Phase Synthesis According to Submonomer Protocol>

Referring to FIG. 7a, the peptoid according to the present disclosure is synthesized on a resin bead through manual synthesis and microwave-assisted solid-phase synthesis. A CEM MARS multimodal microwave reactor (CEM Corp., Matthews, N.C., USA) may be used for the synthesis.

All microwave reactions may be performed under atmospheric pressure and Fmoc-Rink amid MBHA resin (Novabiochem, San Diego, Calif., USA) may be used to prepare a C-terminal amide peptoid. After Fmoc is removed, each monomer is added through bromoacetylation and displacement of bromide with primary amine. The two steps are repeated until the desired peptoid sequence is obtained.

To describe the submonomer synthesis in more detail, Fmoc-Rink amide resin is treated with a mixture of dimethylformamide (DMF) and piperidine to remove the Fmoc.

For bromoacetylation, bromoacetic acid and N,N'-diisopropylcarbodiimide (DIC) are added. The reaction solution is stirred under heating while irradiating microwaves.

To substitute the side chains of the peptoid with desired primary amines, after adding each primary amine to the reaction solution according to the desired peptoid sequence, the reaction solution is stirred under heating.

<Acetylation of N-Terminal Amine of Helical Peptoid>

The acetylation of the N-terminal amine of the peptoid is performed by adding excess amounts of acetic anhydride and pyridine in DMF.

<Removal of Methoxytrityl Through Repeated Treatment of N-Terminal Acetylated Helical Peptoid with Trifluoroacetic Acid (TFA)>

Referring to FIG. 7b, prior to conjugation of porphyrins, the resin-bound peptoid is treated with TFA to remove the Mmt protecting group. TFA solution is added to the resin-bound peptoid while stirring at room temperature. The produced orange solution is discarded and the resin-bound peptoid is washed with DCM. This procedure is repeated 5 times.

<Preparation of Tetraphenylporphyrin (TPP) Carboxylic Acid According to Lindsey's Protocol>

Trichloromethane ($CHCl_3$) is added to a mixture of 4-formylbenzoic acid, benzaldehyde and pyrrole.

Subsequently, $BF_3O(Et)_2$ is added dropwise to the mixture while stirring under nitrogen atmosphere. Then, after sealing the flask with a rubber membrane, the mixture is stirred at room temperature for an hour under nitrogen atmosphere.

Next, after conducting oxidation by adding 2,3-dichloro-5,6-dicyano-1,4-benzoquinone (DDQ), the reaction is terminated by slowly adding triethylamine. Then, the reaction mixture is stirred.

The mixture is concentrated under reduced pressure and the product is washed to obtain tetraphenylporphyrin (TPP) carboxylic acid.

<Preparation of TTP-NHS Ester by Esterification of Tetraphenylporphyrin (TPP) Carboxylic Acid>

The tetraphenylporphyrin (TPP) carboxylic acid is esterified as described in the followings because it is difficult to obtain pure tetraphenylporphyrin (TPP) carboxylic acid with the above-described method.

After mixing N-hydroxysuccinimide, N,N'-dicyclohexylcarbodiimide and tetraphenylporphyrin (TPP) carboxylic acid (5-(4-carboxyphenyl)-10,15,20-triphenylporphyrin), dichloromethane is added. Then, pyridine and 4-dimethylaminopyridine are added to the mixture. The mixture is stirred sufficiently at room temperature. After evaporation using a rotary evaporator, the residue is purified by flash column chromatography (DCM 100%, $R_f$=0.35) to prepare TTP-NHS ester. The TTP-NHS ester is shown in FIG. 7c.

<Conjugation of TPP-NHS Ester with Methoxytrityl-Removed Helical Peptoid>

Referring to FIG. 7b, 1.5 equivalent of TPP-NHS ester is used per amine in general. The TPP-NHS ester is bound to the peptoid through conjugation with the primary amines at the side chains.

After adding the TPP-NHS ester to the resin-bound peptoid in dichloromethane (DCM), N,N-diisopropylethylamine (DIEA) is added and the mixture is stirred under nitrogen atmosphere to prepare a porphyrin-peptoid conjugate.

Subsequently, the porphyrin-peptoid conjugate is separated from the resin using TFA solution. In this way, the porphyrin-peptoid conjugate according to the present disclosure can be prepared successfully.

The method for preparing a porphyrin-peptoid conjugate according to the present disclosure may further include purifying the prepared porphyrin-peptoid conjugate by reversed-phase HPLC.

Since the as-prepared porphyrin-peptoid has low purity, the purity may be improved through reversed-phase HPLC.

EXAMPLES

Example 1

PPC Wherein Distance Between Two Porphyrins is One Pitch

<Preparation of Helical Peptoid by Microwave-Assisted Solid-Phase Synthesis According to Submonomer Protocol>

A peptoid was synthesized on a resin bead through manual synthesis and microwave-assisted solid-phase synthesis. A CEM MARS multimodal microwave reactor (CEM Corp., Matthews, N.C., USA) was used for the synthesis.

All microwave reactions were performed under atmospheric pressure and Fmoc-Rink amid MBHA resin (0.59 mmol/g, Novabiochem, San Diego, Calif., USA) was used to prepare a C-terminal amide peptoid.

The reaction scale was 0.25 mmol (0.42 g of resin).

To remove Fmoc, the Fmoc-Rink amide resin was treated with 20% (v/v) piperidine in dimethylformamide (DMF) (5 mL each) for 60 seconds at room temperature and then treated with microwaves (600 W max power) at 80° C. for 2 minutes. This procedure was repeated twice.

For bromoacetylation, bromoacetic acid (4.18 mL, 1.2 M in DMF, 5 mmol) and N,N'-diisopropylcarbodiimide (DIC) (0.78 mL, 5 mmol) were added. The reaction solution was stirred under and irradiated with microwaves (400 W 15% power) for 2 minutes at 35° C.

For substitution, (S)—N-(1-phenylethyl)glycine (Nspe) (5 mL) or 1,4-diaminobutane protected with (Nlys(Mmt)) (5 mL) was used as a primary amine. The order of addition of the primary amines followed the sequence of Example 1 in Table 1. Nspe means a 2.0 M solution wherein 10 mmol of Nspe is dissolved in NMP. Nlys(Mmt) means a 2.0 M solution wherein 5 mmol of Nlys(Mmt) is dissolved in NMP.

The mixture was irradiated with microwaves (400 W 75% power) for 15 minutes while stirring at 95° C. Between the respective steps, the resin was completely washed with DMF and DCM.

<Acetylation of N-Terminal Amine of Helical Peptoid>

The acetylation of the N-terminal amine of the peptoid was performed by adding excess amounts of acetic anhydride (50 equivalent) and pyridine (55 equivalent) in DMF. For 0.25-mmol reaction scale, acetic anhydride (1.2 mL, 12.5 mmol) and pyridine (1.1 mL, 13.7 mmol) were added to the resin-bound peptoid in DMF (1.5 mL).

<Removal of Methoxytrityl Through Repeated Treatment of N-Terminal Acetylated Helical Peptoid with Trifluoroacetic Acid (TFA)>

Prior to conjugation of porphyrins, the resin-bound peptoid was treated with 0.75% TFA (DCM:TIS:TFA=94.25:5:0.75) to remove the Mmt protecting group. 0.75% TFA solution (6 mL) was added to the resin-bound peptoid while stirring at room temperature for 2 minutes. The produced orange solution was discarded and the resin-bound peptoid was washed with DCM. This procedure was repeated 5 times.

<Preparation of Tetraphenylporphyrin (TPP) Carboxylic Acid According to Lindsey's Protocol>

4-Formylbenzoic acid (16 g), benzaldehyde (2.03 mL) and pyrrole (1.35 mL) were filled in a dried round-bottom flask and then trichloromethane ($CHCl_3$) (with 0.75% ethanol, purchased from Sigma Aldrich, 280 mL) was added.

Subsequently, $BF_3O(Et)_2$ (0.818 mL, 6.66 mmol) was added dropwise to the mixture. The flask was sealed with a rubber membrane and the mixture was stirred at room temperature for an hour under nitrogen atmosphere.

One hour later, 2,3-dichloro-5,6-dicyano-1,4-benzoquinone (DDQ, 4.54 g, 19.98 mmol) was added and oxidation was conducted for 1 hour.

The reaction was terminated by slowly adding triethylamine (1.39 mL, 9.99 mmol). Then, the reaction mixture was stirred for 30 minutes.

The mixture was concentrated under reduced pressure and the resulting dark-purple residue was washed using a silica gel plug to obtain tetraphenylporphyrin (TPP) carboxylic acid.

<Preparation of TTP-NHS Ester by Esterification of Tetraphenylporphyrin (TPP) Carboxylic Acid>

After mixing N-hydroxysuccinimide (56.7 mg, 0.493 mmol), N,N'-dicyclohexylcarbodiimide (101.7 mg, 0.493 mmol) and purified 5-(4-carboxyphenyl)-10,15,20-triphenylporphyrin (approximately 130 mg) to a dried round-bottom flask, dichloromethane (6 mL) was added. Then, pyridine (0.040 mL, 0.493 mmol) and 4-dimethylaminopyridine were added to the flask. The mixture was stirred sufficiently at room temperature. After evaporation using a rotary evaporator, the residue was purified by flash column chromatography (DCM 100%, $R_f$=0.35) to prepare TTP-NHS ester.

<Conjugation of TPP-NHS Ester with Methoxytrityl-Removed Helical Peptoid>

In order to remove residual TFA, the resin-bound, Mmt-removed peptoid (0.0625 mmol) was washed for 1 minute with DCM (4 mL) and DIEA (0.15 mL). After adding the TPP-NHS ester (150 mg, 0.20 mmol) to the resin-bound peptoid in DCM (7 mL), DIEA (0.07 mL, 0.40 mmol) was added.

The reaction mixture was stirred for a day under nitrogen atmosphere. After discarding the reaction mixture, the resin-bound porphyrin-peptoid conjugate was washed cleanly with DMF and DCM.

The resin was separated at room temperature for 10 minutes using a separation solution (DCM:TFA:triisopropylsilane:$H_2O$=50:45:2.5:2.5). After the separation reaction, the solution was filtered using a solid-phase extraction (SPE) cartridge equipped with 20-μm sized hydrophobic polyethylene frit (Applied Separations, Allentown, Pa., USA).

Example 2

PPC Wherein Distance Between Two Porphyrins is Two Pitches

A PPC was prepared in the same manner as in Example 1, except that the addition order of primary amines followed the sequence of Example 2 in Table 1.

Example 3

PPC Wherein Relative Arrangement of Porphyrins is Controlled

A PPC was prepared in the same manner as in Example 1, except that the addition order of primary amines followed the sequence of Example 3 in Table 1.

Example 4

PPC Wherein Distance Between Three Porphyrins is Two Pitches

A PPC was prepared in the same manner as in Example 1, except that the addition order of primary amines followed the sequence of Example 4 in Table 1.

Comparative Examples

Comparative Example 1

Control Peptoid Corresponding to Example 1

<Preparation of Helical Peptoid by Microwave-Assisted Solid-Phase Synthesis According to Submonomer Protocol>

A peptoid was synthesized on a resin bead through manual synthesis and microwave-assisted solid-phase synthesis. A CEM MARS multimodal microwave reactor (CEM Corp., Matthews, N.C., USA) was used for the synthesis.

All microwave reactions were performed under atmospheric pressure and Fmoc-Rink amid MBHA resin (0.59 mmol/g, Novabiochem, San Diego, Calif., USA) was used to prepare a C-terminal amide peptoid.

The reaction scale was 0.25 mmol (0.42 g of resin).

To remove Fmoc, the Fmoc-Rink amide resin was treated with 20% (v/v) piperidine in dimethylformamide (DMF) (5 mL each) for 60 seconds at room temperature and then treated with microwaves (600 W max power) at 80° C. for 2 minutes. This procedure was repeated twice.

For bromoacetylation, bromoacetic acid (4.18 mL, 1.2 M in DMF, 5 mmol) and N,N'-diisopropylcarbodiimide (DIC) (0.78 mL, 5 mmol) were added. The reaction solution was stirred under and irradiated with microwaves (400 W 15% power) for 2 minutes at 35° C.

For substitution, (S)—N-(1-phenylethyl)glycine (Nspe) (5 mL) or 1,4-diaminobutane protected with (Nlys(Mmt)) (5 mL) was used as a primary amine. The order of addition of the primary amines followed the sequence of Comparative Example 1 in Table 1. Nspe means a 2.0 M solution wherein 10 mmol of Nspe is dissolved in NMP. Nlys(Mmt) means a 2.0 M solution wherein 5 mmol of Nlys(Mmt) is dissolved in NMP.

The mixture was irradiated with microwaves (400 W 75% power) for 15 minutes while stirring at 95° C. Between the respective steps, the resin was completely washed with DMF and DCM.

<Acetylation of N-Terminal Amine of Helical Peptoid>

The acetylation of the N-terminal amine of the peptoid was performed by adding excess amounts of acetic anhydride (50 equivalent) and pyridine (55 equivalent) in DMF. For 0.25-mmol reaction scale, acetic anhydride (1.2 mL, 12.5 mmol) and pyridine (1.1 mL, 13.7 mmol) were added to the resin-bound peptoid in DMF (1.5 mL).

<Removal of Methoxytrityl Through Repeated Treatment of N-Terminal Acetylated Helical Peptoid with Trifluoroacetic Acid (TFA)>

Prior to conjugation of porphyrins, the resin-bound peptoid was treated with 0.75% TFA (DCM:TIS:TFA=94.25:5:0.75) to remove the Mmt protecting group. 0.75% TFA solution (6 mL) was added to the resin-bound peptoid while stirring at room temperature for 2 minutes. The produced orange solution was discarded and the resin-bound peptoid was washed with DCM. This procedure was repeated 5 times.

Comparative Example 2

Control Peptoid Corresponding to Example 2

A control peptoid was prepared in the same manner as in Comparative Example 1, except that the addition order of primary amines followed the sequence of Comparative Example 2 in Table 1.

Comparative Example 3

Control Peptoid Corresponding to Example 3

A control peptoid was prepared in the same manner as in Comparative Example 1, except that the addition order of primary amines followed the sequence of Comparative Example 3 in Table 1.

Comparative Example 4

Control Peptoid Corresponding to Example 4

A control peptoid was prepared in the same manner as in Comparative Example 1, except that the addition order of primary amines followed the sequence of Comparative Example 4 in Table 1.

Comparative Example 5

Unstructured Peptoid

A control peptoid was prepared in the same manner as in Example 1, except for the substitution step described below.

For substitution, benzylamine (Npm) (5 mL) or 1,4-diaminobutane protected with mono-Mmt (NLys(Mmt)) (5 mL) was used as a primary amine. The order of addition of the primary amines followed the sequence of Comparative Example 5 in Table 1. Npm means a 2.0 M solution wherein 10 mmol of Npm is dissolved in NMP. NLys(Mmt) means a 2.0 M solution wherein 5 mmol of NLys(Mmt) is dissolved in NMP.

Test Examples

Test Example 1

Measurement of CD Spectra

Figure 8A:
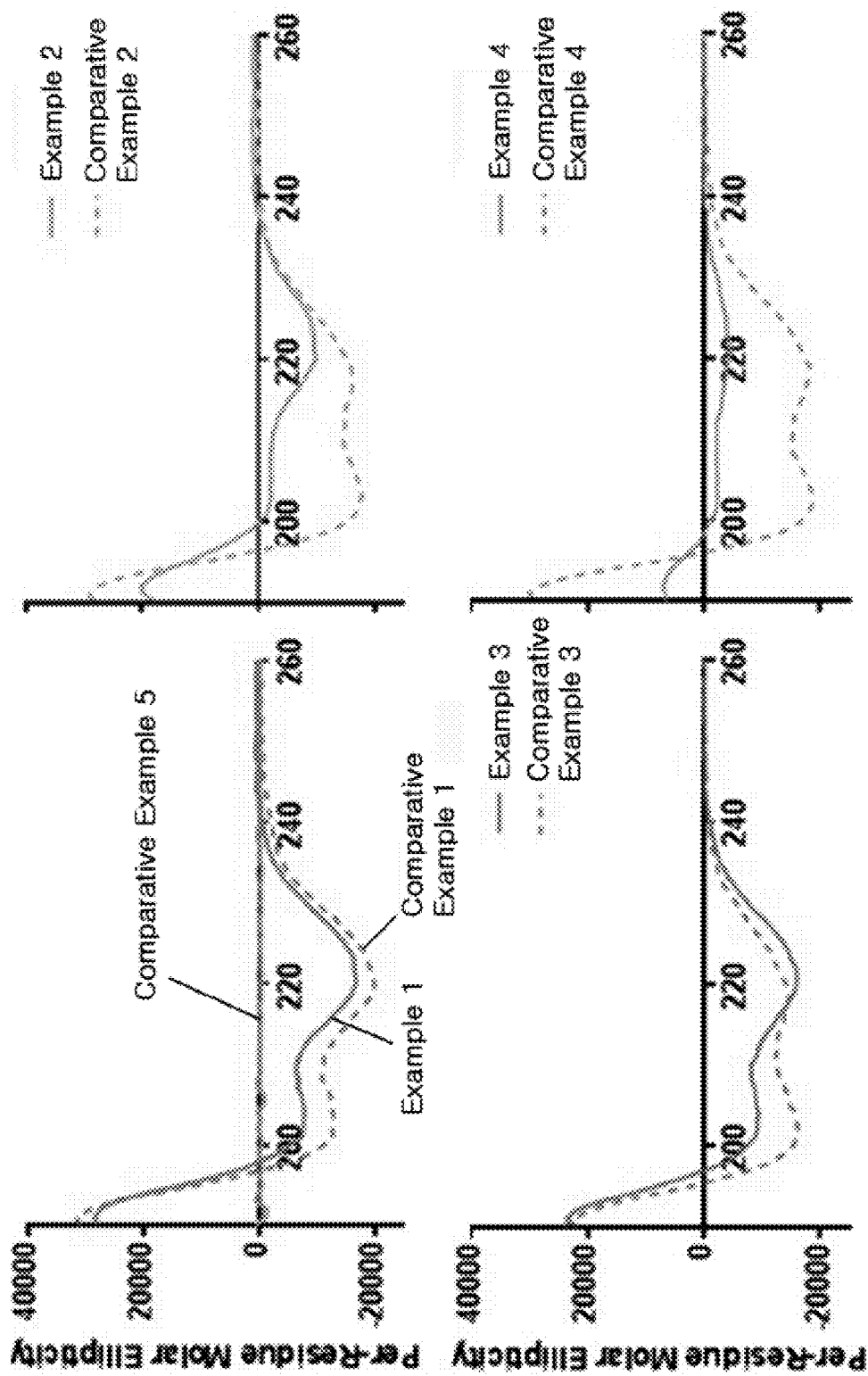
FIG. 8a shows the circular dichroic (CD) spectra of Examples 1-4 and Comparative Examples 1-5 at 190-260 nm.

FIG. 8a shows the circular dichroic (CD) spectra of Examples 1-4 and Comparative Examples 1-5 at 190-260 nm.

Figure 8B:
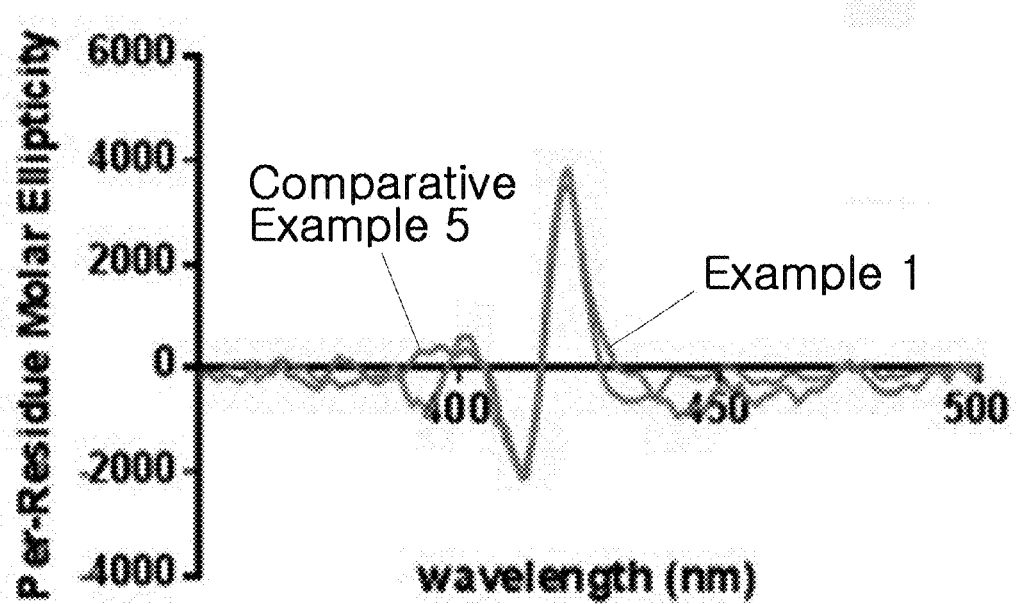
FIG. 8b shows the circular dichroic (CD) spectra of Examples 1-4 and Comparative Examples 1-5 at 350-500 nm.
Figure 8B:
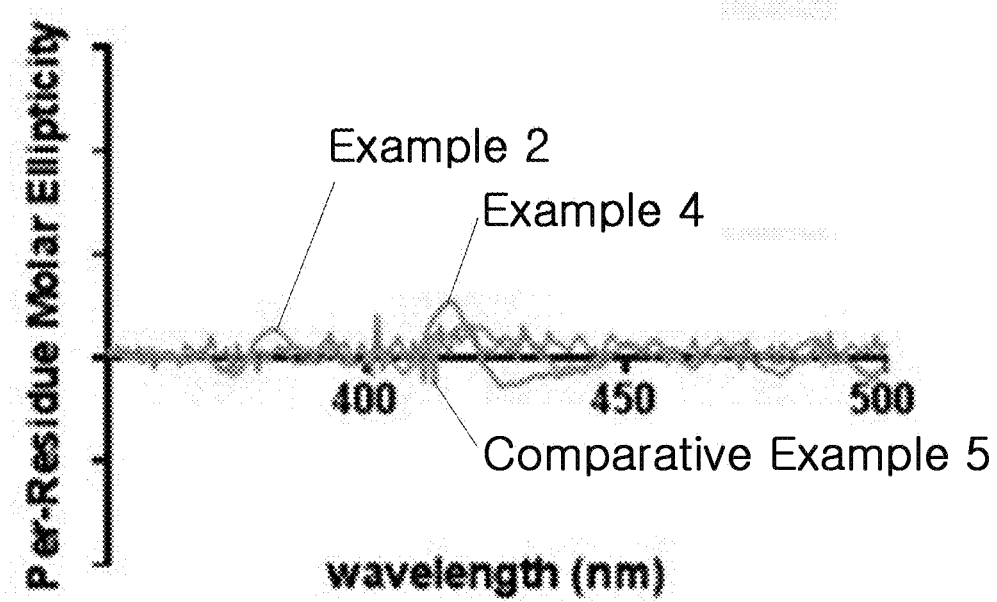

FIG. 8b shows the CD spectra of Examples 1-4 and Comparative Examples 1-5 at 350-500 nm.

The circular dichroic (CD) spectra were measured using the Jasco J-715 spectropolarimeter (Japan Spectroscopic) equipped with a 150-W xenon lamp.

Referring to FIG. 8a, CD spectra were measured at 190-260 nm to investigate carbonyl n→π* (~220 nm) and π→π* (~192 and 202 nm) transitions of the peptoid backbone.

As expected, the control peptoids of Comparative Examples 1-4 without porphyrins showed the typical polyproline type-I (PPI) CD spectra exhibiting two negative Cotton effects.

In Example 1 and Example 3, retained helical folding is observed even after conjugation with porphyrins. In particular, the CD spectrum of Example 3 shows decreased contribution from trans-amide-containing conformers (202 nm) and increased contribution from cis-amide-containing conformers (220 nm). This suggests increased density of the PPI-type helical conformers.

Differently from the nomamers (Example 1 and Example 3), the dodecamers (Example 2 and Example 4) exhibited split helical integrity on the porphyrin conjugate. The structural splitting increased as the number of porphyrins was increased from 2 to 3. It is to be noted that the molecular weight of porphyrins account for about 50% of the total molecular weight of PPC in Example 1, Example 3 and Example 4. Only Example 4 shows severe structural splitting.

The through-space coupling of porphyrins under chiral environment induced exciton-coupled circular dichroism (ECCD), which is confirmed by the bisignate CD signature in the Soret band of porphyrins.

Referring to FIG. 8b, the ECCD spectra of Example 1 and Example 3 show intense Cotton effect signals. This couplet reflects the chirality (molecular asymmetry) between the interacting transition dipole moments of porphyrins.

Example 2, Example 4 and Comparative Example 5 show no or little ECCD effect.

The handedness of peptoid may be defined by the ECCD of PPC. A positive CD couplet (a positive-to-negative pattern going from longer to shorter wavelength) can be interpreted as right handedness.

From the ECCD spectrum, it can be seen that the peptoid consisting of Nspe submonomers forms a right-handed helix.

Judging from the circular dichroic spectra, Example 1 and Example 3 showed either well-retained peptoid helical structure (Example 1) or improved structural stability (Example 3). Also, exciton coupling interactions between porphyrin dyes was confirmed in Example 1 and Example 3.

Test Example 2

Measurement of UV-Vis Absorption Spectra and Color Change

UV-Vis absorption spectra were measured for Examples 1-4, Comparative Example 5 and TPP-ME.

UV-Vis absorption spectra were measured using the Ultrospec 2100 Pro UV/Vis spectrophotometer (GE Healthcare, UK). Samples were dissolved in acetonitrile or chloroform and only the solvent without a peptoid was used as a blank. A 1-mm cuvette was used for the measurement. After preparing a 1.0 mM stock solution, samples of various concentrations were prepared through serial dilution. The absorption spectra were measured at 300-700 nm.

Figure 9A:
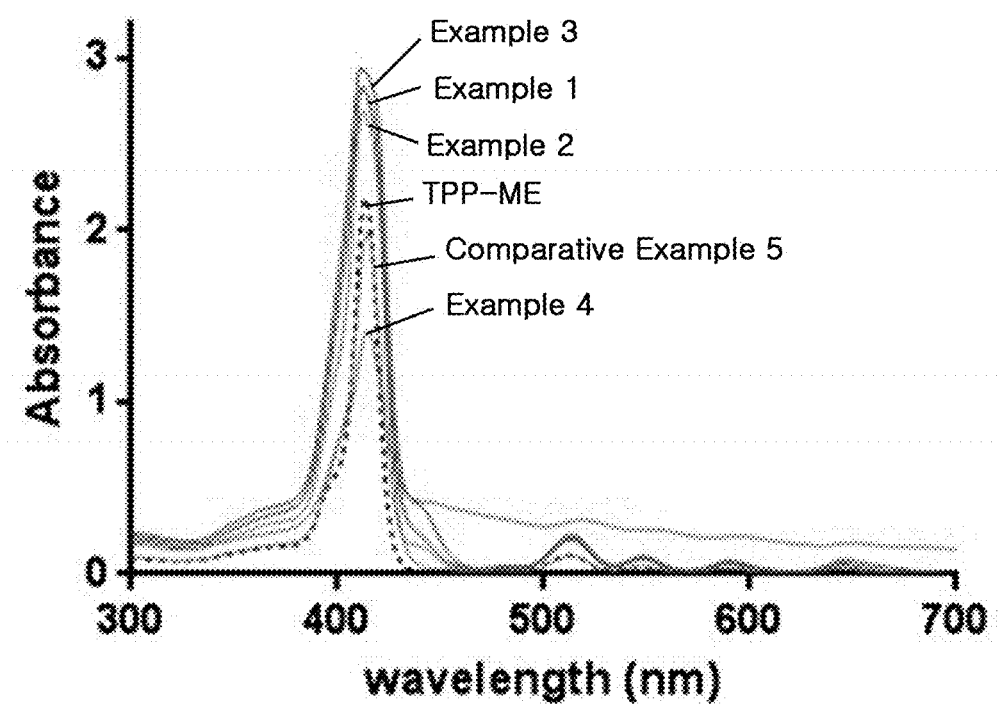
FIG. 9a shows the UV-Vis absorption spectra of Examples 1-4, Comparative Example 5 and TPP-ME.

FIG. 9a shows the UV-Vis absorption spectra of Examples 1-4, Comparative Example 5 and TPP-ME.

Referring to FIG. 9a, similarly to the porphyrin monomers such as TPP-ME (5-(4-methoxycarbonylphenyl)-10,15,20-triphenylporphyrin and tetraphenylporphyrin methyl ester, all the PPCs show intense Soret bands at $\lambda_{max}$=410-415 nm and Q-bands at $\lambda_{max}$=645-650 nm. Examples 1-4 show distinctly wide Soret band widths. In particular, a non-zero absorption coefficient was observed between 400 and 700 nm for Example 4. This means that light harvesting occurs over a wide spectral range.

Figure 9B:
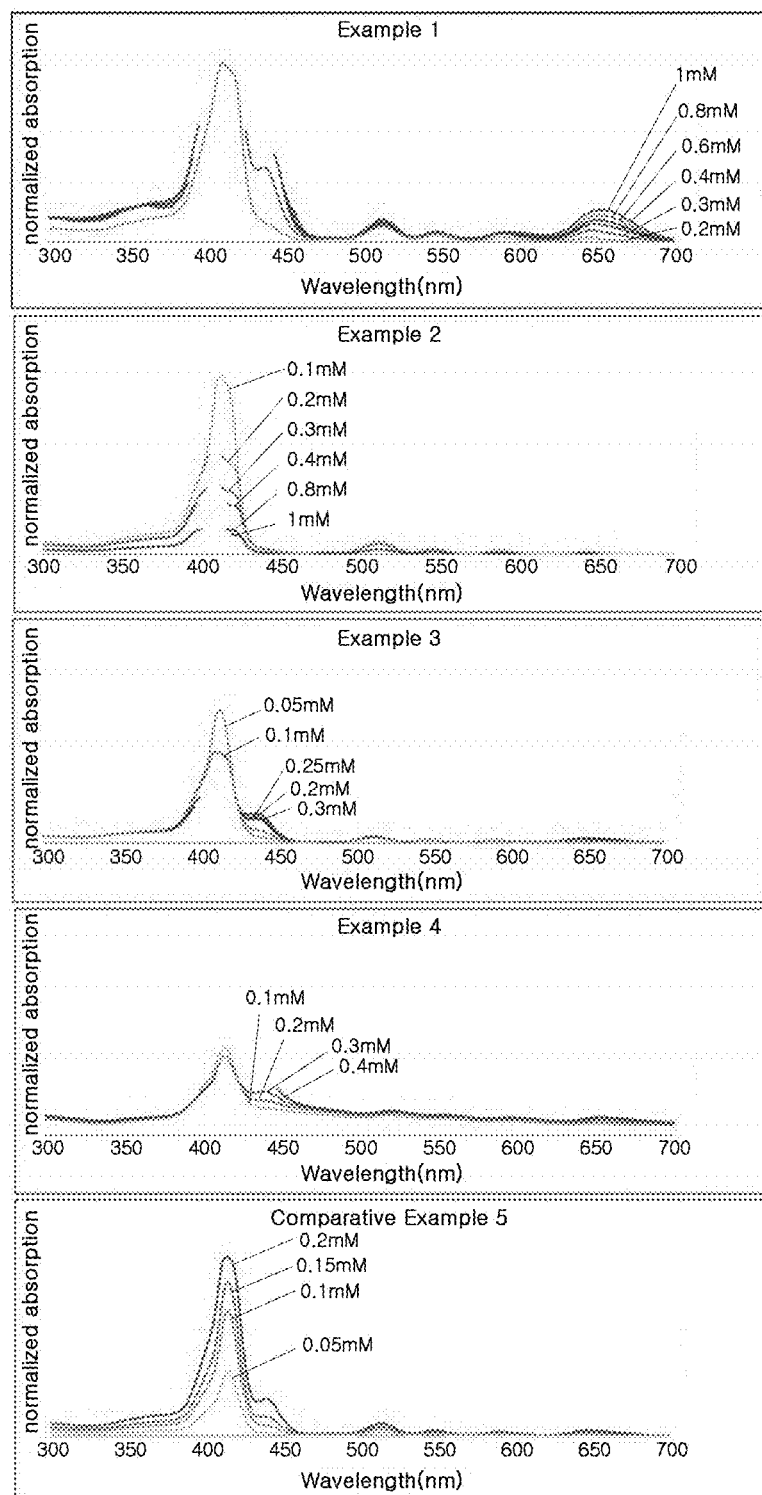
FIG. 9b shows the UV-Vis absorption spectra of Examples 1-4 and Comparative Example 5 with concentration showing shift to longer wavelength.

FIG. 9b shows the UV-Vis absorption spectra of Examples 1-4 and Comparative Example 5 with concentration showing shift to longer wavelength.

Figure 9C:
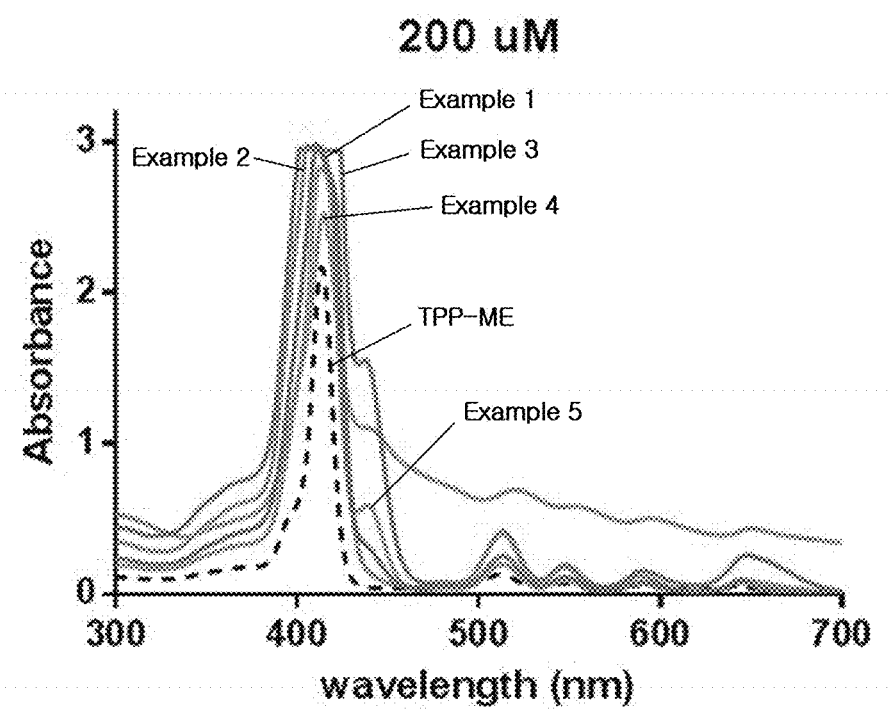
FIG. 9c shows the UV-Vis absorption spectra of Examples 1-4, Comparative Example 5 and TPP-ME (concentration=0.2 mM)

FIG. 9c shows the UV-Vis absorption spectra of Examples 1-4, Comparative Example 5 and TPP-ME (concentration=0.2 mM).

Referring to FIG. 9b, all the conjugates except Example 2 show shift to longer wavelength (red shift) around 438 nm. This shift increases with the concentration of the conjugate solution.

Referring to FIG. 9b and FIG. 9c, Example 2 does not show redshift absorption at high concentrations (up to 1.0 mM) like TPP-ME.

Figure 9D:
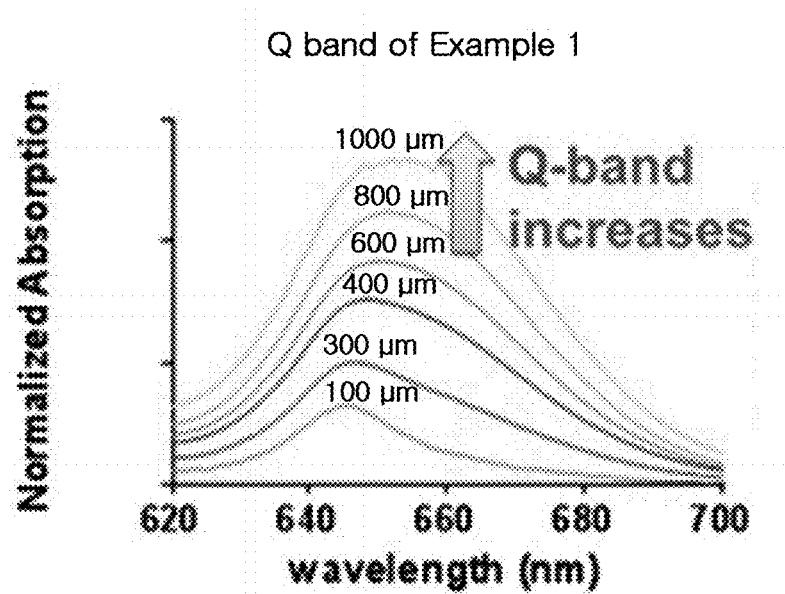
FIG. 9d shows the increase in Q-band of Example 1 with increased concentration.

FIG. 9d shows the increase in Q-band of Example 1 with increased concentration.

Referring to FIG. 9d, strong absorption is observed in the Q-band region near 640-660 nm in Example 1 as the concentration increases.

The concentration-dependent shift to longer wavelength provides the evidence of J-aggregation of in solution and suggests that there occurs not only the exciton coupling of transition dipole moments but also the self-assembly through edge-to-edge interaction.

Figure 9E:
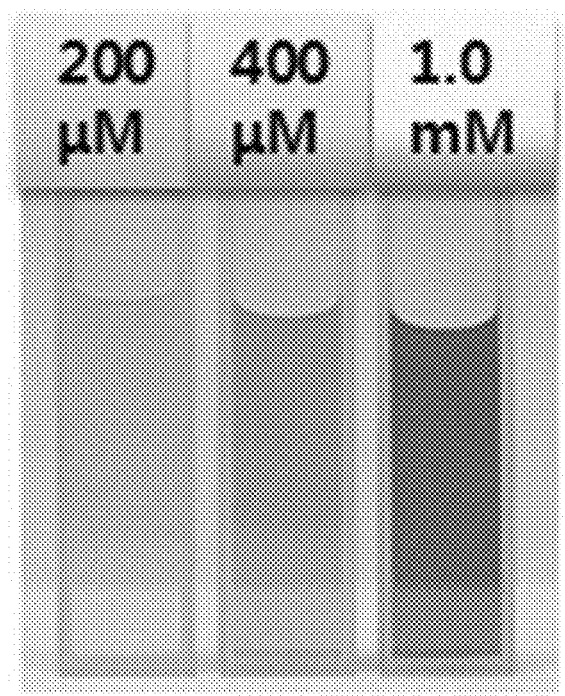
FIG. 9e shows the change in color of Example 1 with concentration.

FIG. 9e shows the change in color of Example 1 with concentration.

Figure 9F:
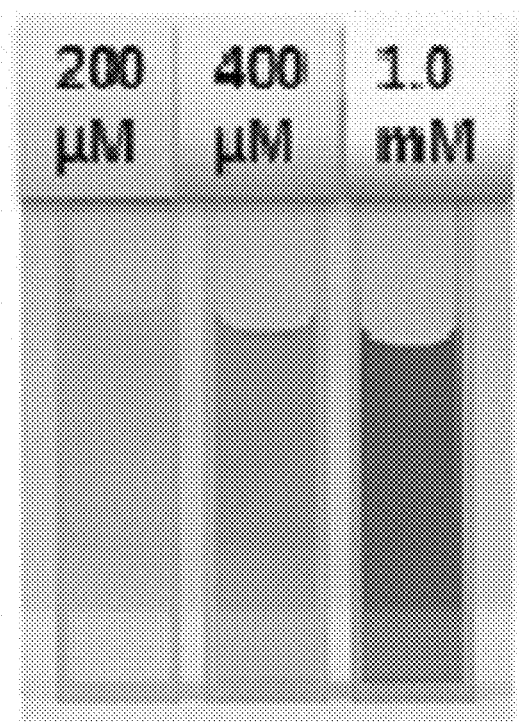
FIG. 9f shows the change in color of Example 3 with concentration.

FIG. 9f shows the change in color of Example 3 with concentration.

Referring to FIG. 9e and FIG. 9f, a distinct color change from green to bright violet is observed when a solution containing the conjugate of Example 1 or Example 3 is diluted. This visually evidences the concentration-dependent redshift absorption and J-aggregation.

In contrast, a solution containing the conjugate of Example 2 retained bright violet color at all concentrations (up to 1.0 mM). Example 4 and Comparative Example 5 show low solubility for acetonitrile. Precipitation occurs in the bright violet solutions containing the conjugates of Example 4 and Example 5 when the concentration increases above 0.2 mM.

From the UV-Vis absorption spectra and color change, it can be seen that intermolecular self-assembly and concentration-dependent redshift of absorption spectra occurred in Example 1 and Example 3.

Test Example 3

Observation of Temperature-Dependent Self-Assembly

Figure 10A:
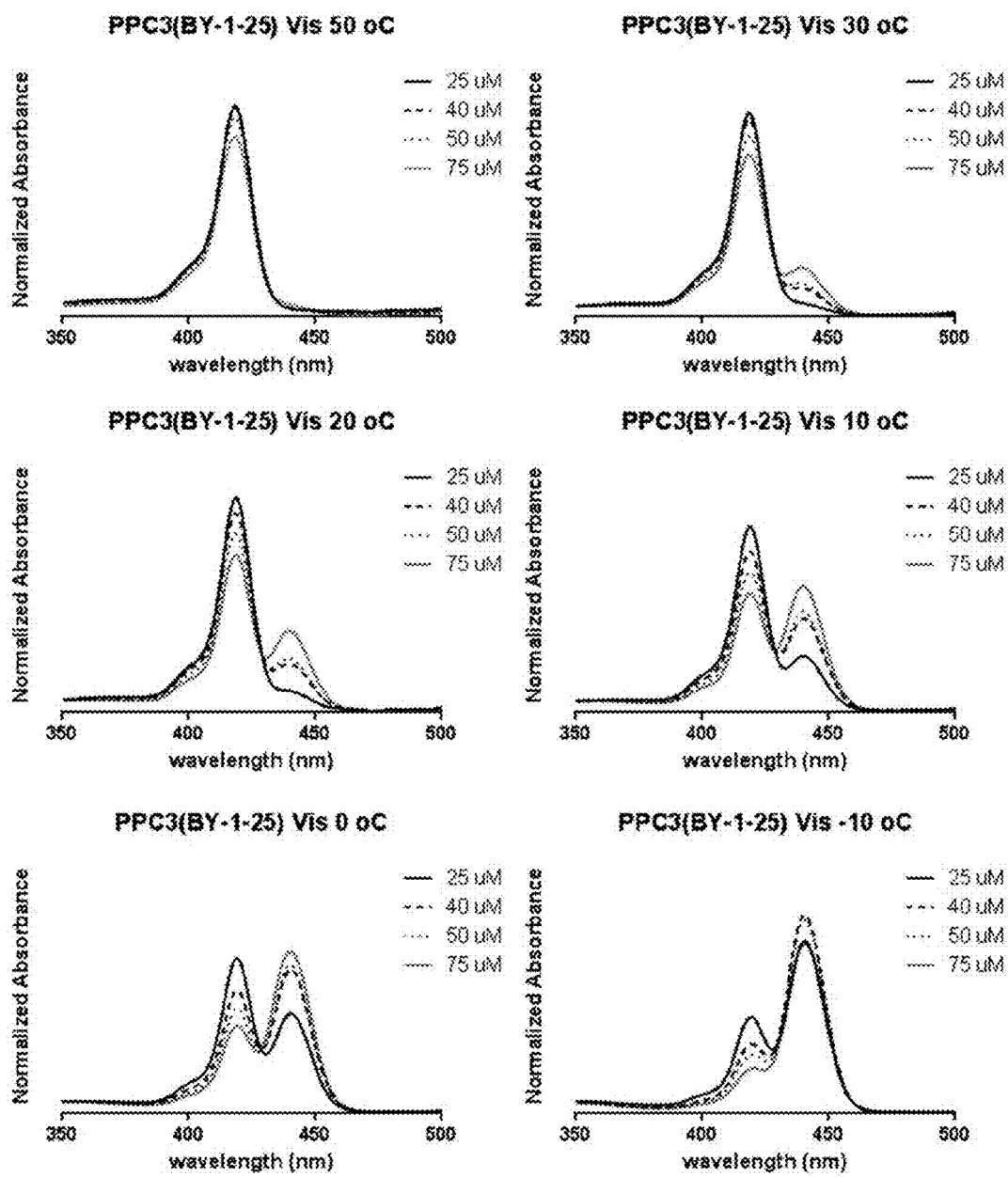
FIG. 10a shows the UV-Vis absorption spectra of Example 3 with temperature.

FIG. 10a shows the UV-Vis absorption spectra of Example 3 with temperature.

Figure 10B:
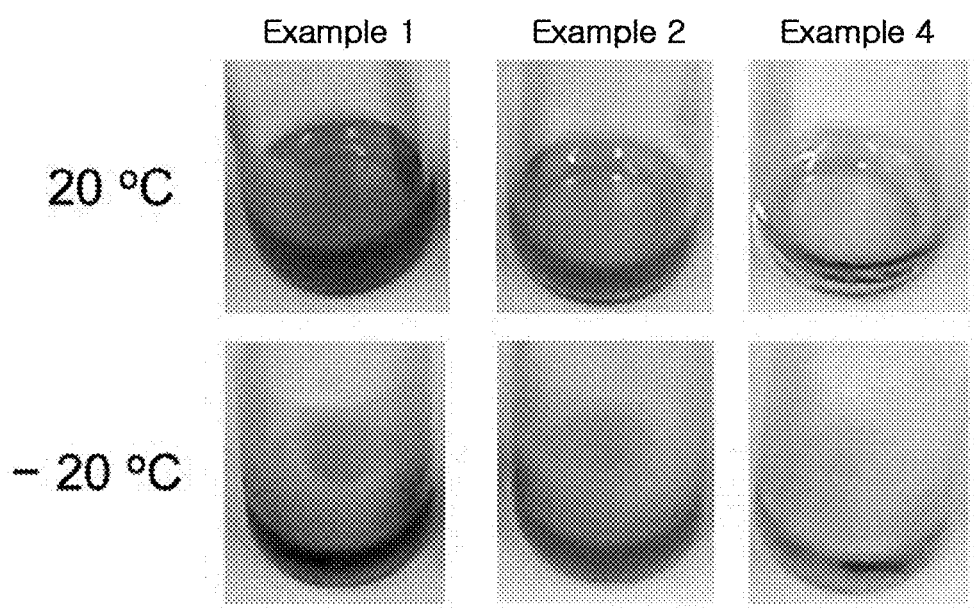
FIG. 10b shows the change in color of Example 1, Example 2 and Example 4 with temperature.

Referring to FIG. 10a, it can be seen that the redshift of UV-Vis absorption spectra of Example 3 increases with concentration at lower temperatures FIG. 10b shows the change in color of Example 1, Example 2 and Example 4 with temperature.

Referring to FIG. 10b, it can be seen that Example 1 shows temperature-dependent color change and self-assembly whereas Example 2 does not. Example 4 exhibits pale green color already at room temperature, because of aggregation of porphyrins.

To conclude, the porphyrin-peptoid conjugate (PPC) of the present disclosure is a system wherein the interactions between porphyrins can be controlled by precisely positioning the dyes on the peptoid backbone and the overall characteristics of the PPC can be controlled also with the characteristics of the peptoid backbone (e.g., helical structure, helical handedness, degree of folding, solubility for solvents, stability, etc.). This molecular scaffold is widely applicable as artificial photosynthesis systems, scaffold of photoelectric materials, sensors and physiologically active materials.

While the present disclosure has been described with respect to the specific embodiments, it will be apparent to those skilled in the art that various changes and modifications may be made without departing from the spirit and scope of the disclosure as defined in the following claims.

What is claimed is:

1. A conjugate represented by Chemical Formula 1, which has a helical structure wherein at least two R groups are $R_2$, and wherein T's are arranged face-to-face:

Chemical Formula 1

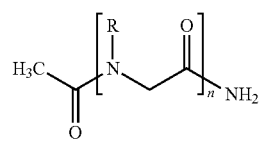

wherein
n is 9 or 12,
R is $R_1$ or $R_2$,
$R_1$ is

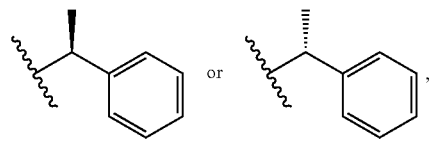

or, $R_2$ is selected from

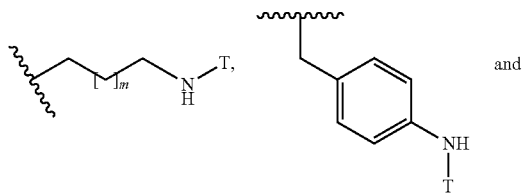

and

-continued
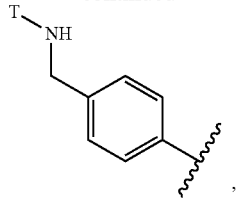
m is an integer from 1 to 5,
T is selected from
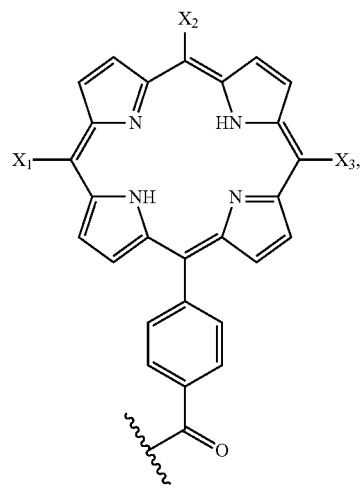
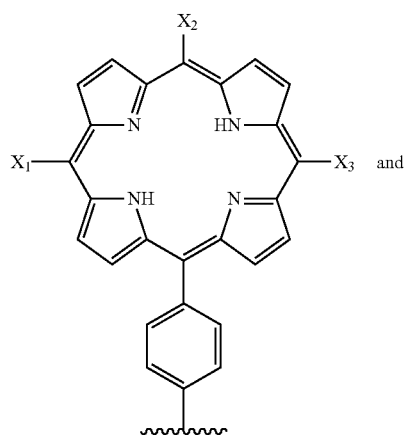 and
-continued
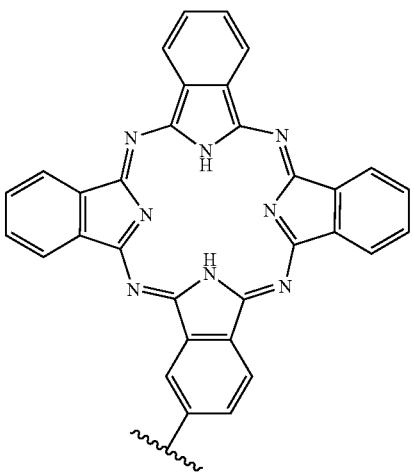
each of $X_1$, $X_2$, $X_3$, which are identical or different, is
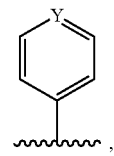
Y is selected from C—H, N, C—COOH, C—$SO_3H$ and C—$NH_2$, and
the tilde symbol indicates a chemical bond.
2. The conjugate according to claim 1, wherein the conjugate has a structure selected from Chemical Formulas 2-5:
Chemical Formula 2
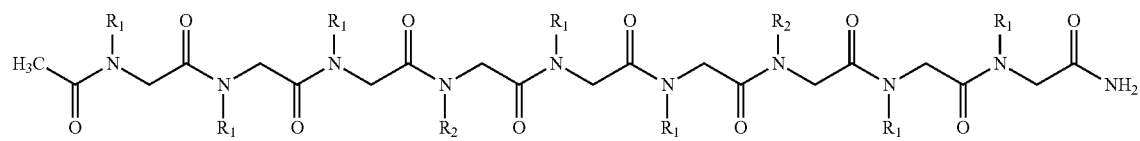
Chemical Formula 3
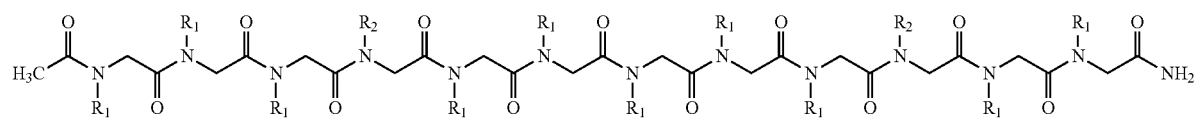

Chemical Formula 4
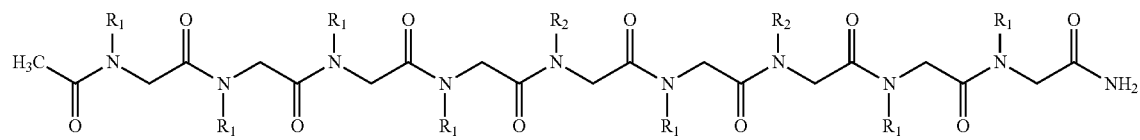
Chemical Formula 5
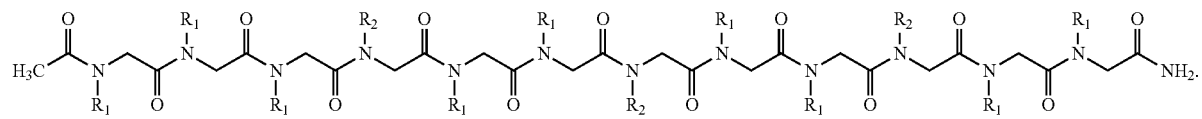
3. The conjugate according to claim 2, wherein the conjugate has a structure selected from Chemical Formulas 6-9:
Chemical Formula 6
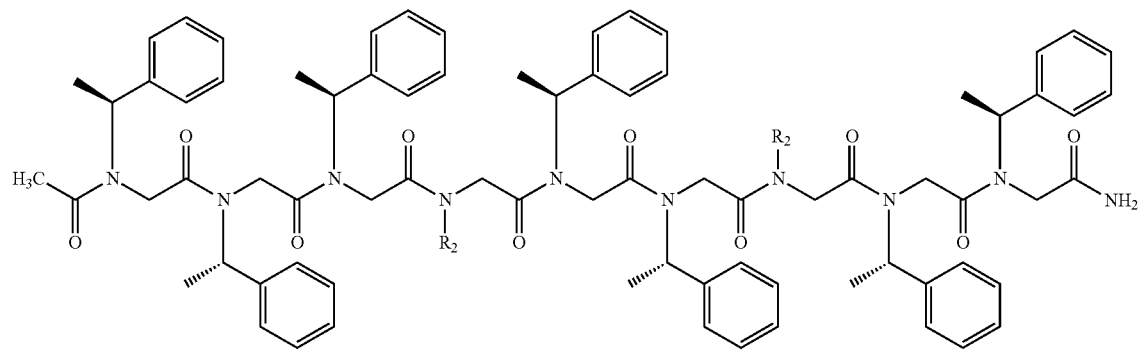
Chemical Formula 7
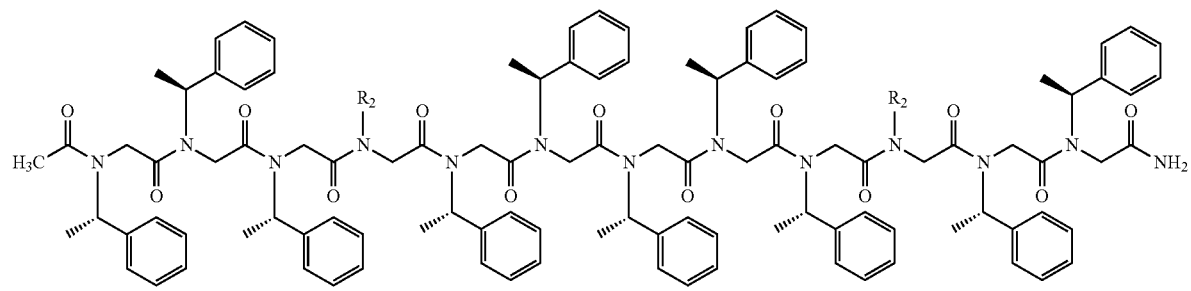
Chemical Formula 8
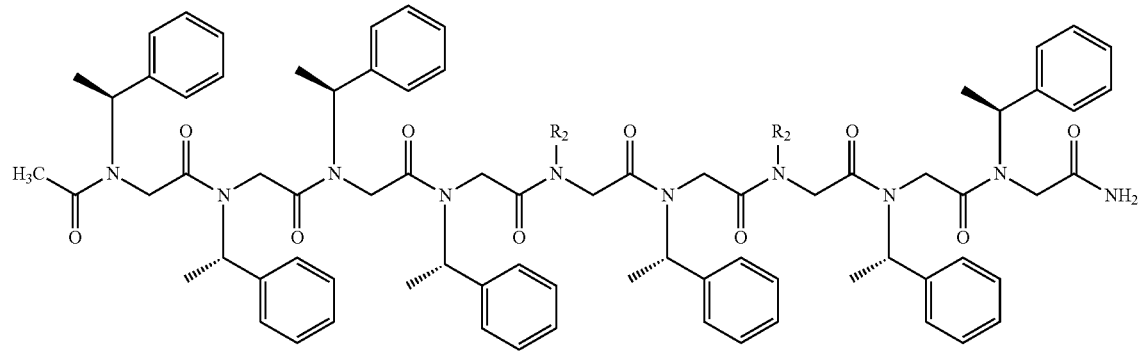

[Chemical Formula 9]
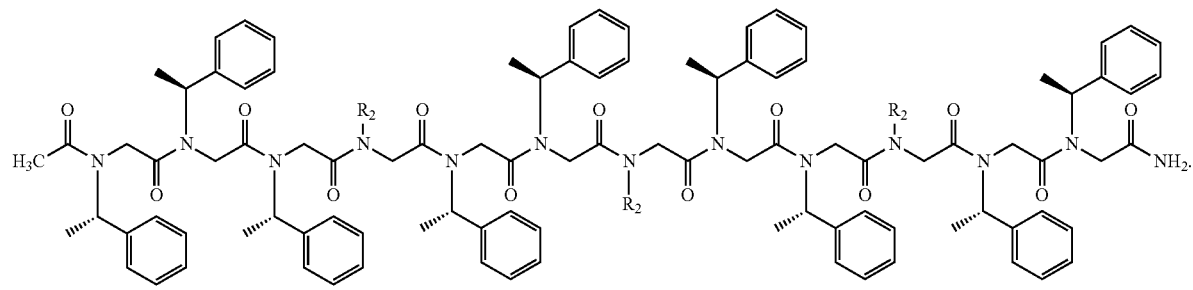
4. The conjugate according to claim 3, wherein R₂'s have the same structure.
5. The conjugate according to claim 1, wherein the conjugate has a structure selected from Chemical Formulas 10-13:
[Chemical Formula 10]
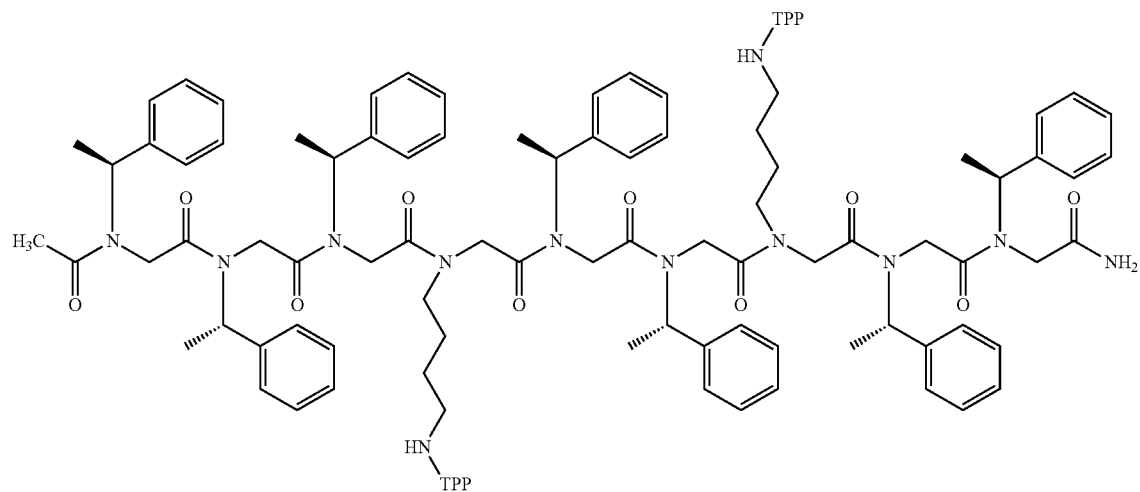
[Chemical Formula 11]
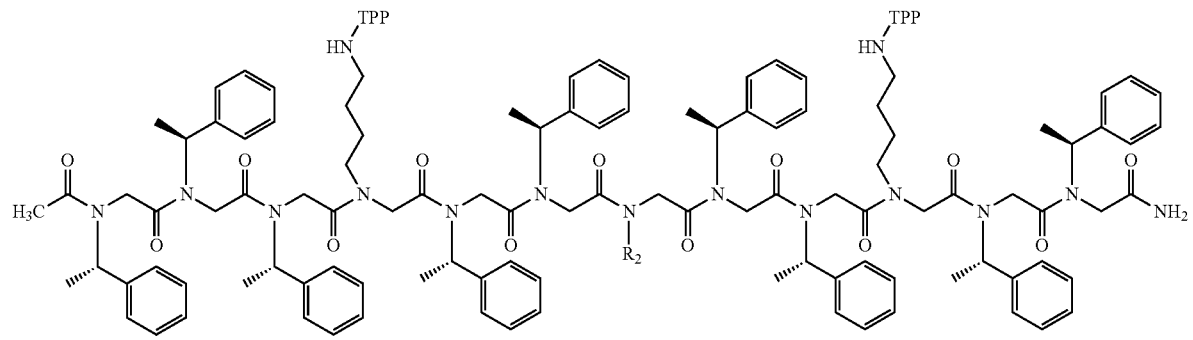

[Chemical Formula 12]

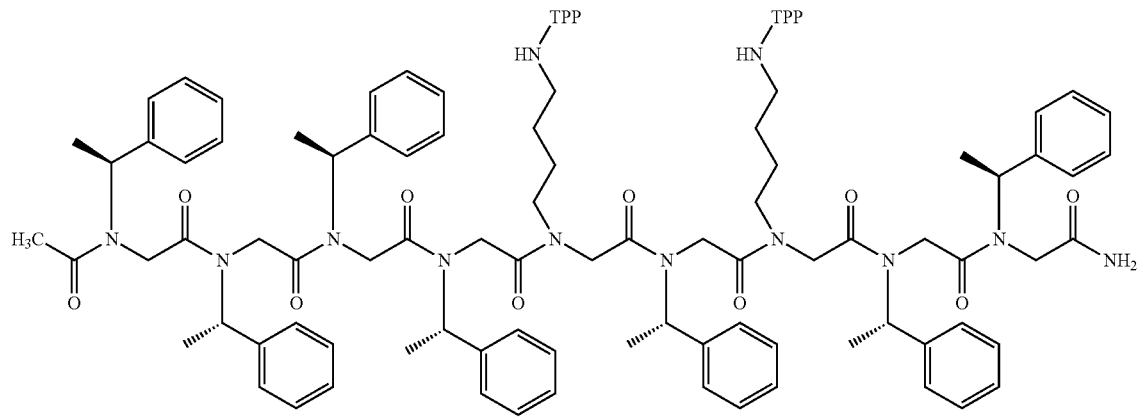

[Chemical Formula 13]

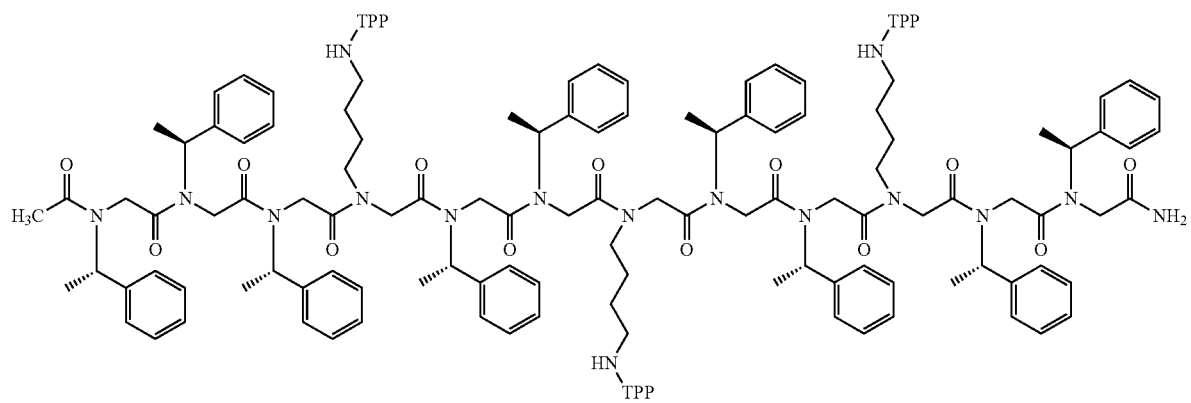

wherein
TPP represents

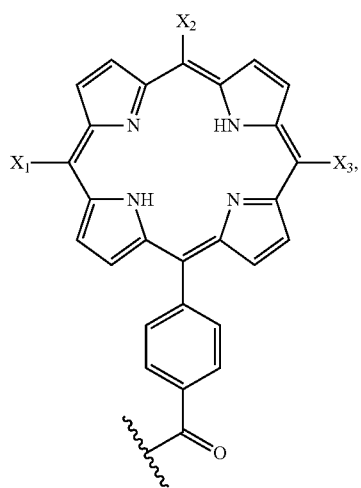

each of $X_1$, $X_2$ and $X_3$ is

Y is C—H, and
the tilde symbol indicates a chemical bond.

6. The conjugate according to claim 1, wherein each R is independently chosen from $R_2$.

7. The conjugate according to claim 1, wherein each R is the same $R_2$.

8. A method for preparing a porphyrin-peptoid conjugate, comprising:
preparing a helical peptoid by microwave-assisted solid-phase submonomer protocol synthesis;
acetylating the N-terminal amine of the helical peptoid;
removing a methoxytrityl group from the N-terminal acetylated helical peptoid by treating repeatedly with trifluoroacetic acid (TFA);
preparing tetraphenylporphyrin (TPP) carboxylic acid according to the Lindsey's protocol;

preparing TTP-NHS ester by esterifying the tetraphenylporphyrin (TPP) carboxylic acid; and
conjugating the TPP-NHS ester with the methoxytrityl-removed helical peptoid.

9. The method for preparing a porphyrin-peptoid conjugate according to claim 8, which further comprises purifying the porphyrin-peptoid conjugate by reversed-phase HPLC.

\* \* \* \* \*